US009833301B2

(12) United States Patent
Fisker et al.

(10) Patent No.: US 9,833,301 B2
(45) Date of Patent: Dec. 5, 2017

(54) METHOD OF MODIFYING THE GINGIVAL PART OF A VIRTUAL MODEL OF A SET OF TEETH

(75) Inventors: Rune Fisker, Virum (DK); Sven Nonboe, Hillerød (DK)

(73) Assignee: 3SHAPE A/S, Copenhagen (DK)

( * ) Notice: Subject to any disclaimer, the term of this patent is extended or adjusted under 35 U.S.C. 154(b) by 177 days.

(21) Appl. No.: 14/000,638

(22) PCT Filed: Feb. 23, 2012

(86) PCT No.: PCT/DK2012/050062
§ 371 (c)(1),
(2), (4) Date: Oct. 8, 2013

(87) PCT Pub. No.: WO2012/113407
PCT Pub. Date: Aug. 30, 2012

(65) Prior Publication Data
US 2014/0032183 A1    Jan. 30, 2014

Related U.S. Application Data

(60) Provisional application No. 61/445,758, filed on Feb. 23, 2011, provisional application No. 61/466,187, filed on Mar. 22, 2011.

(30) Foreign Application Priority Data

Feb. 23, 2011  (DK) ................................ 2011 00126
Mar. 22, 2011  (DK) ................................ 2011 00199
Mar. 22, 2011  (DK) ................................ 2011 00202

(51) Int. Cl.
*G06F 17/50*  (2006.01)
*A61C 13/34*  (2006.01)
(Continued)

(52) U.S. Cl.
CPC .......... *A61C 13/34* (2013.01); *A61C 13/0004* (2013.01); *B33Y 50/00* (2014.12); *B33Y 80/00* (2014.12)

(58) Field of Classification Search
None
See application file for complete search history.

(56) References Cited

U.S. PATENT DOCUMENTS

2002/0048741 A1*  4/2002  Jordan et al. ................... 433/73
2003/0039941 A1*  2/2003  Chishti et al. .................. 433/24
(Continued)

FOREIGN PATENT DOCUMENTS

WO   WO 2009/010543 A1   1/2009
WO      2009/146164 A1  12/2009

OTHER PUBLICATIONS

Klimov, V. E., et al. "A system of solid modeling for low-cost CAD systems." Computers & graphics 12.3-4 (1988): 407-413.*
(Continued)

*Primary Examiner* — Omar Fernandez Rivas
*Assistant Examiner* — Nithya J Moll
(74) *Attorney, Agent, or Firm* — Buchanan Ingersoll & Rooney P.C.

(57) ABSTRACT

Disclosed is a method of generating and modifying a virtual model of a set of teeth, where the method provides that a restoration can be inserted into a physical model of the set of teeth manufactured from the virtual model of the set of teeth.

16 Claims, 15 Drawing Sheets

(51) Int. Cl.
*B33Y 50/00* (2015.01)
*B33Y 80/00* (2015.01)
*A61C 13/00* (2006.01)

(56) References Cited

U.S. PATENT DOCUMENTS

| | | | |
|---|---|---|---|
| 2006/0001739 A1* | 1/2006 | Babayoff | 348/49 |
| 2007/0154868 A1* | 7/2007 | Scharlack et al. | 433/215 |
| 2008/0153067 A1 | 6/2008 | Berckmans et al. | |
| 2008/0294405 A1* | 11/2008 | Kitching et al. | 703/11 |
| 2009/0087817 A1 | 4/2009 | Jansen et al. | |
| 2010/0105011 A1* | 4/2010 | Karkar | A61C 1/084 |
| | | | 433/215 |
| 2010/0114351 A1 | 5/2010 | Kopelman et al. | |
| 2012/0072178 A1* | 3/2012 | Beaudry et al. | 703/1 |

OTHER PUBLICATIONS

International Search Report (PCT/ISA/210) dated Apr. 13, 2012, by the Danish Patent Office as the International Searching Authority for International Application No. PCT/DK2012/050062.

English translation of the Office Action (Notice of Reasons for Rejection) dated Dec. 15, 2015, by the Japanese Patent Office in corresponding Japanese Patent Application No. 2013-554794. (4 pages).

\* cited by examiner

METHOD OF MODIFYING THE GINGIVAL PART OF A VIRTUAL MODEL OF A SET OF TEETH

This invention generally relates to a method of and a system for generating a virtual model of a set of teeth for manufacturing a physical model of the set of teeth, and to a physical model of a set of teeth.

The invention may be used for instance in relation to dental implants and other applications where a restoration is to be inserted into a gingival part of a physical model of the set of teeth.

When designing a dental restoration for a patient, a dental technician often uses a physical model of the patient's set of teeth. In many cases it is preferred that the designed restoration, such as an abutment and the corresponding crown or bridge, is shaped such that it gently displaces a portion of the patient's gingiva. When a physical model of the patient's set of teeth is made in a material which is not easily displaced/deformed by the dental technician, such a design of the restoration will result in that the restoration cannot be inserted into the physical model of the patient's set of teeth.

Disclosed is a method of generating and modifying a virtual model of a set of teeth, said set of teeth comprising a region configured for insertion of a restoration, the region being located in a gingival part of the set of teeth, where the method comprises:
  obtaining at least one three dimensional representation of the set of teeth;
  generating a virtual model of the set of teeth from said three dimensional representation, where the virtual model of the set of teeth comprises a gingival part, said gingival part comprising a virtual region corresponding to said region configured for insertion of a restoration and at least part of the gingiva surrounding said region;
  obtaining a virtual model of said restoration; and
  modifying the gingival part of the virtual model of the set of teeth such that the virtual model of the restoration can be virtually inserted into said virtual region with no overlap between the volume of said virtual model of the restoration and the volume of said gingival part of the virtual model of the set of teeth.

At least a portion of the gingival part of the virtual model of the set of teeth may correspond to the gingival part of the patient's set of teeth.

Disclosed is a method of generating a virtual model of a set of teeth for manufacturing a physical model of the set of teeth, where the method comprises:
  obtaining a three dimensional representation of the set of teeth;
  obtaining a virtual model of a restoration, where at least a sub-gingival part of the virtual model of the restoration is configured to have the shape of an anatomically correct restoration; and
  generating a virtual model of the set of teeth from said three dimensional representation, the virtual model of the set of teeth comprising a gingival part, where the gingival part comprises a gingiva and a region configured for insertion of a restoration, and where the gingival part is configured to provide that when the restoration is inserted in said region the volume of the restoration and the volume of the gingival part do not overlap.

In the context of the present invention, the phrase "sub-gingival part of" used in relation to the restoration may refer to the portion of the restoration which resides below the surface of the gingiva when the restoration is inserted in the virtual or physical model of the set of teeth. The sub-gingival part may be the portion of the restoration arranged below the margin line when the restoration is inserted in the gingival part of the model of the set of teeth.

The sub-gingival part of the restoration may take in different shapes. In some embodiments, the sub-gingival part of a restoration has a cross sectional dimension which changes along the longitudinal direction of the restoration. The cross sectional dimension of the sub-gingival portion of the restoration may increase towards a margin line of the restoration, such that the diameter of the restoration at the margin line is larger than the diameter further below the surface of the gingival part. The cross sectional dimension may be the diameter or area of the restoration in a cross sectional plane which may be perpendicular with the insertion direction of the restoration.

The method may in general relate to a gingival part which is configured to provide that when a restoration is inserted in a region of the gingival part, the volume of the restoration and the volume of the gingival part do not overlap.

The virtual model of the restoration may comprise the entire restoration or a part of the restoration.

In some embodiments, the gingival part of the virtual model generated from the three dimensional representation directly provides that the volume of the restoration and the volume of the gingival part do not overlap. This may be the case e.g. when the method provides that the gingival part is configured for insertion of the restoration in the same step as the virtual model is generated from the three dimensional representation.

In some embodiments, the virtual model of the set of teeth is generated in one step and where the gingival part of the virtual model subsequently is modified to provide that the volume of the restoration and the volume of the gingival part do not overlap. This may be the case e.g. when the method provides that the gingival part is configured for insertion of the restoration after the virtual model is generated from the three dimensional representation.

In some embodiments, the gingival part of the virtual model of the set of teeth is modified to provide that the adjoining surfaces of the virtual model of the restoration and the gingival part of the virtual model of the set of teeth follow each other.

In some embodiments, an offset is provided between the adjoining surfaces of the virtual model of the restoration and the gingival part of the virtual model of the set of teeth. The offset may be substantially uniform over a part of said sub-gingival part of the restoration.

In the context of the present invention, the phrase "adjoining surfaces" may be used in relation to virtual surfaces which are adjoining e.g. when the virtual model of the restoration is arranged in its anatomical correct position relative to the virtual model of the set of teeth. The phrase may also be used in relation to the surfaces of a restoration formed from the virtual model of the restoration when this arranged at a physical model of the set of teeth.

In some embodiments, modifying the gingival part of the virtual model of the set of teeth comprises digitally cutting a portion of the gingiva away such that the volume of the restoration and the volume of the gingiva do not overlap. The digital cutting away may correspond to a removal of material from a physical model of the set of teeth. Preferably, the digitally cutting away is made with the virtual model of the restoration virtually arranged in the gingival part of the virtual model of the set of teeth.

One advantage that may be provided by the present invention is the possibility of digitally combining a restoration with a gingival part of a virtual model of a set of teeth, where the anatomically correct shape of the restoration is taken into account.

One advantage that may be provided by the present invention is that a anatomically correct restoration can be inserted into a physical model manufactured from a virtual model of the set of teeth generated using the method according to the present invention. The restoration may be arranged in its anatomically correct position and at the anatomically correct orientation relative to the gingival part and any neighboring teeth in the model. This may allow e.g. a dental technician to test the form and arrangement of the actual restoration in a physical model of the set of teeth.

Disclosed is a method of generating and modifying a virtual model of a set of teeth for manufacturing a physical model of the set of teeth, where the method comprises:
  obtaining a three dimensional representation of the set of teeth;
  generating a virtual model of the set of teeth from said three dimensional representation, the virtual model of the set of teeth comprising a gingival part comprising a gingiva; and
  modifying the gingival part to enable insertion of a restoration in a region of the virtual model configured for insertion of a restoration.

Disclosed is a method of generating a virtual model of a set of teeth for manufacturing a physical model of the set of teeth, where the method comprises:
  obtaining a virtual model of the set of teeth, the model comprising a gingival part comprising a gingiva; and
  obtaining a virtual model of a restoration configured to be arranged in its anatomical correct position relative to said gingival part of the model;
where the surface of the gingiva defines a first surface at said restoration; and
  modifying the gingiva at said restoration such that the surface of the modifying gingiva defines a second surface at said restoration, wherein the second surface is configured to avoid an overlap between the volume of the restoration and the volume of the gingival part of the model.

Disclosed is a method of adjusting a virtual model of a set of teeth, where the virtual model of the set of teeth is for manufacturing a physical model of the set of teeth, where the method comprises:
  obtaining a pre-adjustment configuration of a virtual model of the set of teeth, the virtual model of the set of teeth comprising a gingival part; and
  obtaining a virtual model of a restoration configured to be arranged in its anatomical correct position relative to said gingival part of the model,
where the volume of the gingival part of the virtual model of the set of teeth and the volume of the restoration overlaps when the restoration is arranged in the anatomical correct position; and
  adjusting a portion of the gingival part of the virtual model of the set of teeth arranged at said restoration providing a post-adjustment configuration of the virtual model of the set of teeth, in which post-adjustment configuration the gingival part of the model is configured to avoid overlap between the volume of the virtual model of the restoration and the volume of the gingival part of the model of the set of teeth.

Disclosed is a method of adjusting a virtual model of a set of teeth, where the virtual model is for manufacturing a physical model of the set of teeth, where the method comprises:
  obtaining a pre-adjustment configuration of a virtual model of the set of teeth, the model comprising a gingival part; and
  adjusting a portion of the gingival part of the model arranged at said restoration providing a post-adjustment configuration of the virtual model of the set of teeth, in which post-adjustment configuration the gingival part of the model is configured to avoid overlap between the volume of a restoration configured to be arranged in its anatomical correct position in the gingival part of the model.

In some embodiments, the adjusting of the gingival part comprises configuring the shape of the gingival part such that the overlap between the volumes is avoided.

In some embodiments, the method comprises configuring the material of the gingiva at the restoration to be sufficiently soft such that a restoration may deform the gingival part. This may be done by removing relative harder material from a physical model of the set of teeth and replacing it by a relative softer material, such as replacing gypsum with a dental silicone material.

Disclosed is a method of generating a physical model of a set of teeth, where the method comprises:
  obtaining at least one three dimensional representation of the set of teeth;
  generating and modifying a virtual model of the set of teeth from said at least one three dimensional representation, the virtual model of the set of teeth comprising a gingival part; and
  modifying the gingival part to enable insertion of a restoration in a region of the virtual model of the set of teeth configured for insertion of a restoration.
  manufacturing said physical model from said virtual model of the set of teeth.

In some embodiments, the method comprises configuring the gingival part to avoid an overlap with a restoration when the restoration is inserted in the model. Such an overlap may make it difficult or even impossible to arrange the restoration in its anatomical correct position in the gingival part of the model.

Disclosed is a physical model of a set of teeth, wherein the physical model is manufactured from a virtual model generated by the method according to the present invention.

In the context of the present invention, the phrase "a restoration" may refer to a full dental restoration or a part of a restoration, such as an abutment or a crown arranged on said abutment. An abutment may be a cutmized abutment or a stock-abutment.

At least one step of the method is computer implemented. In some embodiments at least the generating and modifying of the virtual model of the set of teeth is computer implemented.

In some embodiments, a first three dimensional representation of the set of teeth is obtained by scanning the patient's set of teeth with a scan body arranged in said implant region. Data relating to the scan body may hence become part of the virtual model of the set of teeth.

In some embodiments, said virtual model of the set of teeth is generated at least in part from said first three dimensional representation. The virtual model of the set of teeth may thus comprise a section corresponding to the gingival part of the set of teeth.

In some embodiments, a second three dimensional representation of the set of teeth is obtained by scanning the patient's set of teeth with the emergence profile at said implant region being visible. In this case, may data relating to the emergence of the gingiva be derived or become part of a virtual model of the set of teeth.

In some embodiments, said virtual model of the set of teeth is generated at least in part from said second three dimensional representation. The virtual model of the set of teeth may then comprise a section corresponding to the gingival part.

In some embodiments, one of said first or second three dimensional representation of the set of teeth is obtained by scanning a relatively larger section of the patient's set of teeth, and the other of said first or second three dimensional representation then is obtained by scanning a relatively smaller section around the implant region.

In some embodiments, the method comprises generating a first virtual model of the set of teeth from said first three dimensional representation of the set of teeth.

In some embodiments, the method comprises generating a second virtual model of the set of teeth from said second three dimensional representation of the set of teeth.

In some embodiments, the method comprises combining the first and second virtual models of the set of teeth to generate said virtual model of the set of teeth. Such a virtual model of the set of teeth may then comprise both the emergence profile and data relating to the implant position and orientation.

In some embodiments, a virtual model of the scan body is provided and virtually aligned with the first virtual model of the set of teeth to determine the orientation and position of the implant.

In some embodiments, the restoration is designed based on the virtual model of the set of teeth.

In some embodiments, the restoration is a pre-manufactured restoration such as a pre-manufactured abutment.

In some embodiments, the modified virtual model of the set of teeth is for manufacturing a physical model of the set of teeth.

In some embodiments, at least a sub-gingival part of the virtual model of the restoration is configured to have the shape of an anatomically correct restoration.

The region of the virtual model configured for insertion of a restoration may comprise a region of the gingival part configured to comprise an implant analog, a hole, a healing abutment, a scan-body or in principle any dental indication. The region may be bounded by an area of the gingiva surface having a circumference which is bounded partly by the nearest neighbor teeth.

In some embodiments, the method comprises configuring the gingiva mask to comprise an opening, where the opening is configured to allow a restoration to access the gingival part arranged below the gingiva mask.

In some embodiments, a virtual hole is provided in said gingival part of the virtual model of the set of teeth.

The virtual hole may be such that a corresponding hole in the physical model of the set of teeth is configured to mate with a part of said restoration configured to fit into the gingival part of the physical model of the set of teeth. The virtual hole may be configured to allow an implant analog to inserted manually in the corresponding hole of the physical model of the set of teeth.

The virtual hole and/or said implant analog may be configured such that said the implant analog can be inserted only in the correct anatomical position and orientation in the gingival part of the model.

The opening of the gingiva mask may be aligned with an implant analog arranged in the gingival part below the gingiva mask In some embodiments, the implant analog is configured to have a shape with reduced cross sectional rotation symmetry, such as an N-fold symmetry, wherein N is an integer number below 25.

The implant analog may have no rotation symmetry in its cross sectional plane.

In some embodiments, the gingival part of the virtual model of the set of teeth is configured to provide that a corresponding ejection hole in the physical model of the set of teeth is in fluid connection with said hole such that a restoration or an implant analog can be accessed through said ejection hole to be ejected from the gingival part of the physical model of the set of teeth.

In some embodiments, the implant analog is configured to comprise a stop section with a smaller cross sectional area at its distal end, said stop section preferably being arranged centrally around the longitudinal axis of the implant analog.

In some embodiments, the implant analog is configured to comprise a stop surface at its distal end, said stop surface preferably being arranged centrally around the longitudinal axis of the implant analog.

In some embodiments, the stop surface is reduced in size/diameter compared to other parts of the implant analog to provide that space is provided for rounded corners of the hole side wall.

The virtual hole defined in the gingival part of the virtual model of the set of teeth may be configured to provide that the corresponding hole in the physical model of the set of teeth has rounded edges at its distal end or at any kink along the longitudinal direction of the hole.

In some embodiments, a height inspection groove is defined in the implant analog to allow for a visually or a contact based inspection of whether the implant analog is arranged in the correct position in the gingival part of the model.

The height inspection groove may extend around the entire circumference of the implant analog forming a band shaped height inspection groove which can be seen from all directions in a cross sectional plane intersecting the height inspection groove.

A window or a through hole may be provided in the gingival part to allow visual and/or physical contact to the inplant analog from the outside of the model. The window or through hole may be provided in the virtual model or after the manufacturing of the physical model.

In the context of the present invention, the phrase "below" is only used to describe the relative orientation of the parts of the model and does not present a limitation on which part is closer to the ground than the other parts. One part being below another part may be used to describe an arrangement of the parts relative to the occlusion plane of a set of teeth.

The phrase "below" may be used to describe that a sub-gingival part of a virtual model of a restoration is arranged behind the surface of the gingival part relative to a viewpoint situated at a position corresponding to the center of a patient's mouth. That is, in a patient's mouth the object which is arranged below the surface of the gingival part of the set of teeth may not be visible.

In the context of the present invention, the phrases "proximal end" and "distal end" may refer to two opposite ends of a e.g. a holed in the gingival part of the model, where the distal end may refer to the part of said hole which is the furthest away from the entrance of the hole. The distal end may also be referred to as the bone end.

In some embodiments, the virtual model comprises a restoration configured to be inserted in the virtual model at the region configured for insertion of a restoration.

In some embodiments, the restoration comprises a full restoration or a part of a restoration, such as an abutment or a crown arranged on said abutment, an implant bar, or in principle any other indication used in relation to dental restorations.

In some embodiments, restoration is to be arranged in its anatomical correct position relative to said gingival part of the model.

In some embodiments, configuring the gingival part provides that the restoration can be positioned in a physical model manufactured from the virtual model, the restoration even in the case where the surface of the gingival part of the virtual model generated from three dimensional representation and an adjoining surface of the restoration overlaps.

In the context of the present invention, the phrase "the model" may be used in relation to both the physical and the virtual manifestation of the set of teeth. In some embodiments, there is a one-to-one relationship between the virtual model and the physical model of the set of teeth.

In some embodiments, configuring the gingival part comprises modifying the gingival part of the virtual model generated from the three dimensional representation.

The virtual representation of the set of teeth may be provided by scanning the set of teeth, such as by scanning the set of teeth by means of an intraoral scanner or by scanning an impression of the set of teeth.

In some embodiments, a unit, such as a healing abutment, a scan-body or an implant analog, is arranged in the region configured for the insertion of a restoration during the scanning of the set of teeth. The generated virtual model of the set of teeth may hence show such a unit. The method may comprise digitally removing this unit from the virtual model or it may comprise generating a virtual model of the set of teeth where such a unit is not part of the virtual model.

In some embodiments, configuring the gingival part comprises configuring the material of the gingival part at the restoration to be sufficiently soft such that a restoration may deform the gingival part. In a physical model manufactured from the virtual model, the material may be sufficiently soft such that an operator, such as a dental technician, may arrange the restoration in its anatomical correct postion without having to use excessive force.

In some embodiments, configuring or modifying the gingival part comprises virtually removing a portion of said gingival part in the region configured for insertion of a restoration.

The configuring the gingival part of the model may comprise digitally cutting a portion of the gingiva away such that the volume of the restoration and the volume of the gingiva do not overlap.

After a removal of material from the model, the gingival part in a physical model manufactured from the virtual model is configured to follow the adjoining surface of the restoration such that a correct positioning of the restoration is enabled. This may correspond to cutting the gingiva to the restoration, i.e. that the gingival part of the model adapts to the restoration. In this embodiment, the entire gingival part of the model may be manufactured in a relatively hard material since there is no overlap between the volumes of the gingival part of the model and the restoration when the latter is positioned correctly in the model.

In the context of the present invention, the phrase "to follow the adjoining surface of the restoration" may refer to the case the restoration is arranged in relation to the gingival part such that at least a part of the sub-gingival portion of the restoration has a surface which is substantially parallel to the adjoining surface of the gingival part. The adjoining surfaces of the sub-gingival portion of the restoration and the gingival part may be spaced apart by a substantially constant distance over a least part of their common area, such that there is a substantially constant offset between the sub-gingival portion of the restoration and the gingival part over that area. The adjoining surfaces may be taken to be the area of the side-walls of a hole in the gingival part, where said hole is configured for the insertion of a restoration. The side walls may be the surface of such a hole that is located along the direction of insertion of the restoration into the gingival part.

In some embodiments, the method comprises virtually adding material to the gingival part of the virtual model in the region configured for insertion of a restoration. The virtual addition of the material may occur after a virtual removal of material in the region configured for insertion of a restoration.

In some embodiments, the gingival part of the virtual model of the set of teeth defines a first surface at the region configured for insertion of a restoration.

In some embodiments, the first surface follows at least a section of said emergence profile of the gingiva in the region.

In some embodiments, modifying the virtual model of the set of teeth comprises replacing said first surface by a second surface, where said second surface is shaped such that the virtual model of said restoration can be virtually arranged in said virtual implant region with no overlap with the modified virtual model of the set of teeth.

In some embodiments, at least a section of said second surface is defined by offsetting part of the surface of the virtual model of the restoration. The offset may be such that the second surface encloses the surface of the virtual model of the restoration.

In some embodiments, the method comprises subtracting the virtual model of the restoration or the volume enclosed by the offset surface from the virtual model of the set of teeth. The second surface may then be identical to or be based on the virtual surface of the gingival part from which a volume is subtracted.

In some embodiments, the gingival part of the virtual model of the set of teeth after the virtual removal of a portion of the gingiva defines the second surface at the region configured for insertion of a restoration. The second surface may be referred to as a cutting surface. Cutting the gingival part at the second surface may correspond to cutting the gingival part to the restoration.

In some embodiments, the gingival part of the virtual model of the set of teeth after virtually adding material to the gingiva defines a third surface at the region configured for insertion of a restoration.

The third surface may be substantially identical to said first surface.

The first, second and third surfaces are provided on the virtual model of the set of teeth. In a virtual model, the surfaces may be defined as a result of the generation of the gingival part of the model. In a physical model, the surfaces may be realized when the volume of the gingival part of the model is manufactured.

In some embodiments, the gingival part of the virtual model of the set of teeth is divided into a first and a second gingival region by the second surface, where said second gingival region is arranged between the second surface and the third surface, the second surface forming an interface between the first and the second gingival region.

The first gingival region may be configured to be manufactured in a first material in a physical model manufactured from the virtual model.

In some embodiments, the method comprises manufacturing the physical model of the set of teeth such that the portion of the physical model corresponding to the first gingival region of the virtual model of the set of teeth is manufactured in a first material.

The second gingival region may be configured to be manufactured in a second material in a physical model manufactured from the virtual model.

In some embodiments, the method comprises manufacturing the physical model of the set of teeth such that the portion of the physical model corresponding to the second gingival region of the virtual model of the set of teeth is manufactured in a second material.

In some embodiments, the second material is configured to be softer than the first material at ambient conditions. The indention hardness of the second material may be smaller than that of the first material.

The second material is configured to be comprised in a removable unit in a physical model manufactured from the virtual model. The addition of material to the gingival part of the model may comprise generating a gingiva mask.

The gingiva mask may be produced in a relatively hard material and may be moved before arranging the restoration in the model such that an overlap between the gingival part and the restoration may be avoided by removing the gingiva mask before positioning the restoration.

The gingiva mask may be configured to comprise a first retention structure configured to mate with a second retention structure arranged on the gingival part of the model, such that the gingiva mask is arranged correct when said first and second retention structures mate.

In some embodiments, the gingival part of the model comprises an undercut region, in which said second gingival region is partly confined.

In some embodiments, a void is provided between the adjoining surfaces of the restoration and the gingival part of the model.

In some embodiments, the method comprises that the teeth of the model are manufactured in a relatively harder, less flexible material and at least the gingival of the model around the restoration is manufactured in a relatively softer, more flexible material.

It may be an advantage to manufacture the teeth of the model in a relatively harder material and the gingival part of the model in a relatively softer material, because then the different materials resemble the real materials in the mouth, and this facilitates the testing or modeling of the restoration.

The second material may be configured to be softer than the material used to manufacture the restoration.

The material of the physical model may be gypsum which often is used for physical models of teeth, or a relatively harder material used for 3D printing of a physical model. The second material may be a softer and more compressible dental silicone.

Disclosed is a cover for enclosing a volume in cooperation with a physical model of a set of teeth, where said cover is for use when filling said volume with a second gingival material, said cover comprising an implant engaging portion;
a top portion comprising a model facing surface and a through channel, where one part of the model facing surface is configured for contacting the physical model of the set of teeth and and second part if configured for enclosing said volume in collaboration with the surface of the physical model, and where said through channel provides a liquid connection to the enclosed volume.

In some embodiments, the method comprises providing a cover which in cooperation with the first gingival region is configured to enclose the second gingival region.

The cover may comprise an opening configured to allow the injection of said second material into said second gingival region in a physical model manufactured from the virtual model of the teeth.

The cover may be configured to have a surface facing said second gingival region, which surface may be shaped as said third surface.

When the cover is arranged in relation to the physical model, the model facing surface defines the surface of the second gingival region when the enclosed volume between the cover and the physical model is filled with a material which is sufficiently soft and compressible such that an operator with reasonable effort can deform it by pressing the restoration into the material. The cover defines said third surface.

In some embodiments, the implant engaging portion of the cover is dimensioned according to the implant analog in the physical model.

In some embodiments, the model facing surface of the cover is linked to the abutment, such that for a particular abutment, the surface is such that the generated third surface is shaped according to the corresponding surfaces of the abutment.

In some embodiments, the method comprises designing and configuring the model to be manufactured by means of a specific manufacturing process.

In the context of the present invention, the phrase "cross sectional" may refer to a plane which is perpendicular to the longitudinal direction. The cross sectional shape of e.g. an implant analog element may be the shape of the implant analog in such a plane intersecting the base.

In some embodiments, the model comprises two or more restorations. The method according to the present invention may evidently be applied to any number of restorations in a set of teeth, such as two, three, four or more restorations.

In some embodiments, the method comprises obtaining a virtual representation of a set of teeth and forming a virtual model of said set of teeth from said virtual representation.

In some embodiments, the virtual representation of the set of teeth is provided by scanning the set of teeth by means of an intraoral scanner or by scanning an impression of the set of teeth. The virtual representation of the set of teeth may comprise a point cloud.

Thus the virtual model and afterwards the physical model may be created based on scanning e.g. an impression instead of e.g. creating a model by casting the model from an impression. An advantage of this embodiment is that better accuracy is obtained, because the impression itself is scanned instead of scanning a casted or poured model, in which defects may have emerged, when making the model. Furthermore, it may be an advantage that the manual and time consuming work of making the model in gypsum from the impression is avoided. Thus this embodiment provides a simpler and possibly faster and cheaper process.

A reason for manufacturing a physical model from the impression is that dental technicians may prefer to have a physical model to work with when they adapt the dental restoration(s) for a patient.

The impression can then be scanned to create a representation of both the lower and upper part of the jaws. Thereby the virtual model is automatically generated in software based on the scanning of the impression.

In some embodiments, the method comprises removing further portions of the model corresponding to the gingiva, such that it becomes easier for a user to take e.g. an implant analog out of the physical model.

In some embodiments, the method comprises applying a scan of the entire set of teeth so that the antagonist is visualized, and providing a virtual articulator, so that the entire set of teeth can be occlusion tested.

In some embodiments, the method comprises manufacturing the physical model by means of three dimensional printing or milling.

Examples of 3D printing or milling are:
- inkjet-like principle, where it is possible to manufacture the outer part of the physical model in a high quality and/or an expensive material, and the inner part can be manufactured in a cheaper material, such as e.g. wax;
- standard 3D printing;
- standard 3D milling;
- steriolithography (SLA), which is a type of rapid prototyping process;
- selective laser sintering (SLS), which is a type of rapid prototyping process.

In some embodiments, the method comprises designing and adapting the model to be manufactured by means of a specific manufacturing process.

For example different materials can be chosen for manufacturing of the physical model.

In some embodiments, the restoration or a unit which the restoration is a part of, is manufactured such that the restoration is positioned in the physical model corresponding to the position of the real, anatomical teeth in the mouth of the patient.

In some embodiments, the correct anatomical position of the restoration is with regard to the height relative to the model, with regard to the horisontal position which can be controlled by ensuring that the restoration cannot rotate when placed in the model.

When the restoration is arranged to have an anatomical correct height relative to the gingival part of the model, a crown of the restoration may be arranged correctly relative to the horizontal plane of the teeth model.

The physical model of the set of teeth may be used by a dental technician to build up a model of the restoration, which may be known as the wax modulation. The model of the restoration or the wax modulation may then be used to cast the actual restoration, which is for example made of a metal material, such as a metal crown with porcelain veneering.

The physical model may be used to check whether a manufactured restoration actually fits the physical restoration in the physical model.

Even if the restoration is produced by CAD/CAM, it is still advantageous to check that the produced restoration has a correct fit by checking the restoration on the physical model. There are several steps in the manufacturing process, so potentially something could go wrong in one of the steps, and then it is better that the dental technician discovers and corrects a fault before the restoration is send to the dentist and inserted in the patient's mouth.

If the restoration is produced from a material which can change shape or size, e.g. zirconium dioxide also known as zirconia, it is also an advantage to check the restoration after production, because the material may then shrink or become crooked during and/or after the heating process.

If the restoration is produced manually and/or when the porcelain work on the restoration is performed manually, then the dental technician needs a model of the other teeth in the set of teeth to check that there is space enough between the neighbor teeth for the restoration and that the shape of the porcelain match the neighbor teeth.

If the model is manufactured by 3D printing, many models can be manufactured simultaneously compared to e.g. manufacturing by milling.

In some embodiments, the method comprises digitally repositioning the gingival part of the model around the restoration, such as digitally repositioning the gingival part before manufacturing the physical model of the set of teeth.

This repositioning may be an advantage because often it is a problem that when a tooth is prepared in the mouth of the patient, then so much of the tooth is grinded away, whereby the soft, compliant gingival tissue around the prepared tooth will adjoin or follow or collapse to the new reduced shape of the prepared tooth instead of remaining in the original shape following the non-prepared tooth. So when e.g. the impression of the prepared tooth is made, then the gingiva is adjoining the prepared tooth and the manufactured model of the teeth will then have a gingiva adjoining the restoration, and thus there may be no space between the gingival and the restoration to model and place a restoration. But when repositioning, removing, or relocating the gingival part of the model around the restoration then there is space for the restoration and the veneering, e.g. porcelain, which the dentist may add after having inserted the restoration in the mouth of the patient.

In some embodiments, digitally repositioning the gingival part of the model comprises digitally moving the gingival part of the model away from to the restoration.

The digital repositioning the gingival part of the model may comprise moving the gingiva adjoining the restoration.

In some embodiments, digitally repositioning the gingival part of the model comprises digitally moving the gingival part of the model outwards relative to the restoration.

It may be an advantage that the gingival part of the model may be moved without changing the size of gingiva, which is important since the gingival in the mouth of the patient also will only change shape and move but not change size, i.e. the gingival does not become bigger or smaller, it only changes shape.

It may be an advantage that if the model of the restoration is designed using CAD, then it can be derived from the CAD program how much the gingiva on the teeth model should be moved in order to fit the modeled restoration.

The method comprises manufacturing the physical model by means of three dimensional printing or milling.

In some embodiments the physical model may be manufactured using a casting mold for casting an at least partly soft mould as part of the physical model of the set of teeth.

The casting mold may be adapted to be manufactured by means of rapid prototyping, such as 3D printing A casting mold CAD model may be generated as an impression of at least a part of the virtual model, said casting mold CAD model thereby comprising the negative geometry of the set of teeth.

A physical model may be manufactured from a virtual model of the set of teeth generated and modified by the method according to the present invention.

In some embodiments, the method comprises providing that the model comprises a side ejection hole through which the restoration in the physical model can be contacted and ejected from its cavity.

The hole may be arranged in the gingival part of the model.

It may be an advantage that when providing an ejection hole in the side on the model, then this hole is accessible from the side, which may be an advantage when e.g. mounting the model on an articulator, where the side of the model can be accessed as opposed to the bottom of the model which is attached to the articulator. Therefore it may be an advantage to arrange the ejection hole on the side of the model instead of in the bottom of the model. However, a hole, e.g. an ejection hole, may alternatively and/or additionally be arranged in the bottom of the model.

In some embodiments, the method comprises providing that the restoration comprises a hole adapted to be arranged in continuation of the side ejection hole in the model, when the restoration is arranged in the cavity of the model.

It may be an advantage that when providing a hole in the side of the model and a hole in the restoration, then when the two holes are aligned, i.e. arranged in continuation of each other, or arranged end to end, then the restoration is arranged correctly relative to the model.

Whether the hole in the restoration and the hole the in model are aligned can be checked by means of visual inspection or by using a tool adapted to fit into the holes. Thus when the tool can move trouble-free through the hole in the model and into the hole in the restoration, then the alignment of the restoration in the model will be correct. In some embodiments, the side ejections hole is arranged such that the tool can move the entire way through both the model and the restoration, thus the tool is inserted on one side of the model and can pass through the model to the other side of the model. Thus in some embodiments, the side ejection hole is arranged such that a tool can pass through a section of the model comprising both the restoration and the gingival part of the model surrounding the cavity in which the restoration is arranged, such that the tool can be inserted on one side of the section and can pass through the section to a side of the section arranged opposite to the restoration.

In some embodiments, the method comprises arranging the hole in the model as a through hole passing from the surface of model to the cavity for the restoration, and arranging the hole in the restoration as a blind hole.

The through hole may be passing from the gingival part of the model. The hole in the restoration may be arranged as a blind hole in a position corresponding to the root of the restoration.

In some embodiments, the method comprises arranging the hole in the model as a through hole passing from the surface of model to the cavity for the restoration, and arranging the hole in the restoration as a through hole.

The through hole may be passing from the gingival part of the model. The hole in the restoration may be arranged as a through hole in a position corresponding to the root of the restoration.

Thus the hole in the restoration may be a through hole passing the entire way through the restoration to the other side of the cavity. In this case the hole in the model may then pass through the entire model, i.e. passing from the surface of the model to one end of the cavity inside the model, and from the other end of the cavity through the model to the other surface of the model.

It may be an advantage to have a side ejection hole which is a through hole in both the model and the restoration, since then the positioning of the restoration in the model can be checked by visual inspection, which may be facilitated when there is a free passage through the entire model and restoration.

Furthermore, it may be an advantage for the manufacturing of the model and the restoration to produce the side ejection holes a through holes. For example, the model and restoration can be manufactured by means of jet printing, and for example a soft support material may be arranged in the model and the restoration at places where there should be no material in the final version. When the manufacturing of the model or the restoration has been completed, the support material will be removed, e.g. washed away, melted away or digged away. In this case it may be easier to remove all the support material from a hole if the hole is a through hole instead of a blind hole.

In some embodiments, the method comprises arranging the restoration in the gingival part of the model such that the restoration is adapted to be inserted in and removed from the gingival part of the model without conflicting with or being blocked by the neighbor teeth in the model.

In some embodiments, the method comprises arranging the restoration in the model such that the insertion direction of the restoration corresponds to the insertion direction of the real, anatomical tooth in the set of teeth.

In some embodiments, the method comprises arranging the restoration in the gingival part of the model such that the insertion direction of the restoration is so skew that the restoration is adapted to be inserted in and removed from the gingival part of the model without conflicting or being blocked by the neighbor teeth in the model.

In some embodiments, the method comprises determining an insertion path for the restoration. The insertion path may be according to the insertion direction at the implant.

In some embodiments, the method comprises identifying a circumference line for the restoration. The circumference line may be defined as the outer circumference of the restoration when the virtual model of the restoration is viewed along the insertion direction or insertion path. When having defined an offset surface from the virtual model of the restoration, the circumference line may be defined as the outer circumference of the offset surface when the offset surface is viewed along the insertion direction.

In some embodiments, an extrusion volume is defined by the insertion direction and the circumference line. The extrusion volume defines the volume through which the restoration travels when being inserted into the gingival part of the virtual model of the set of teeth or when removed therefrom.

The orientation extrusion volume may have a direction which differs slightly from the insertion direction. This may be the case over some sections of the extrusion volume when the extrusion volume is defined by the circumference line and an insertion path which in these sections differ from the insertion direction determined at the gingival part.

In some embodiments, the method comprises providing that an implant analog configured to be positioned e.g. in the gingival part of the model comprises a stop surface functioning as a stop for the implant analog when it is positioned in the gingival part, such that the implant analog is hindered from being pushed further into the gingival part of the model than the correct anatomical height of the implant analog corresponds to.

In some embodiments, the stop surface is plane and horisontal.

The stop surface may be plane and horisontal relative to the rest of the model, and/or relative to the insertion direction of the implant analog in the gingival part etc.

It may be an advantage that the stop surface is plane and horizontal since this may provide an optimal positioning and support of the implant analog in the model.

In the context of the present invention, the phrase "horizontal" may refer to a plane which is substantially parallel to the occlusion plane of the patient's dentition.

In some embodiments, the method comprises that when the model is 3D printed, at least part of the stop surface is horisontal with respect to the remainder of the model.

Thus the overall form of the stop surface may be sloping, slanting or inclined, but each single printing layer should be horisontal so the sloping surface will be made up of several small horisontal parts. This provides a very good set fit.

If the model is milled instead of 3D printed, then the stop surface may not be horisontal, but can be in any direction.

In some embodiments, the method comprises that the stop surface is arranged in a printing layer which is also present in the remainder of the model.

It may be an advantage because the stop surface is then level with the bottom part of the implant analog, whereby the implant analog can be pushed down exactly to the right layer in the model, whereby the position of the implant analog in the model is anatomically correct with respect to the height of the implant analog in the physical model.

Thus the stop layer is at a height h which is h=n×printing layer thickness.

In some embodiments, the method comprises providing that one or more adjacent teeth in the model are adapted to be removably inserted in the model.

An advantage is that when the adjacent or neighbor teeth can be removed from the model, then it may be easier for the dental technician to build up the model of a restoration, since then there is free space around these teeth, e.g. on all or some of the sides.

The physical model may be manufactured using a casting mold for casting an at least partly soft mould as part of the physical model of the set of teeth, where the casting mold is adapted to be manufactured by means of rapid prototyping, such as 3D printing. A casting mold CAD model is generated as an impression of at least a part of the virtual model, said casting mold CAD model thereby comprising the negative geometry of the set of teeth. At least one sectioning of the casting mold CAD model may be defined by means of at least one separation plane and/or separation spline.

Disclosed is also a computer program product comprising program code means for causing a data processing system to perform the method, when said program code means are executed on the data processing system, and a computer program product comprising a computer-readable medium having stored there on the program code means.

According to another aspect, disclosed is also an ejection tool for ejecting a restoration arranged in a physical model of a set of teeth.

In some embodiments, the ejection tool comprises an elongated component which is adapted to fit into a through hole in the gingival part of the model.

In some embodiments, the ejection tool is adapted to fit into a blind hole and/or a through hole in the restoration.

The present invention relates to different aspects including the method described above and in the following, and corresponding methods, devices, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

In the following description, reference is made to the accompanying figures, which show by way of illustration how the invention may be practiced.

In FIGS. 1, 2, 3, 5 and 7 an abutment for a dental implant is used as an illustrative example of a dental restoration. The restoration may evidently also consist of or comprise other parts such as a crown, a bridge, a removable denture, or a denture.

Figure 1:
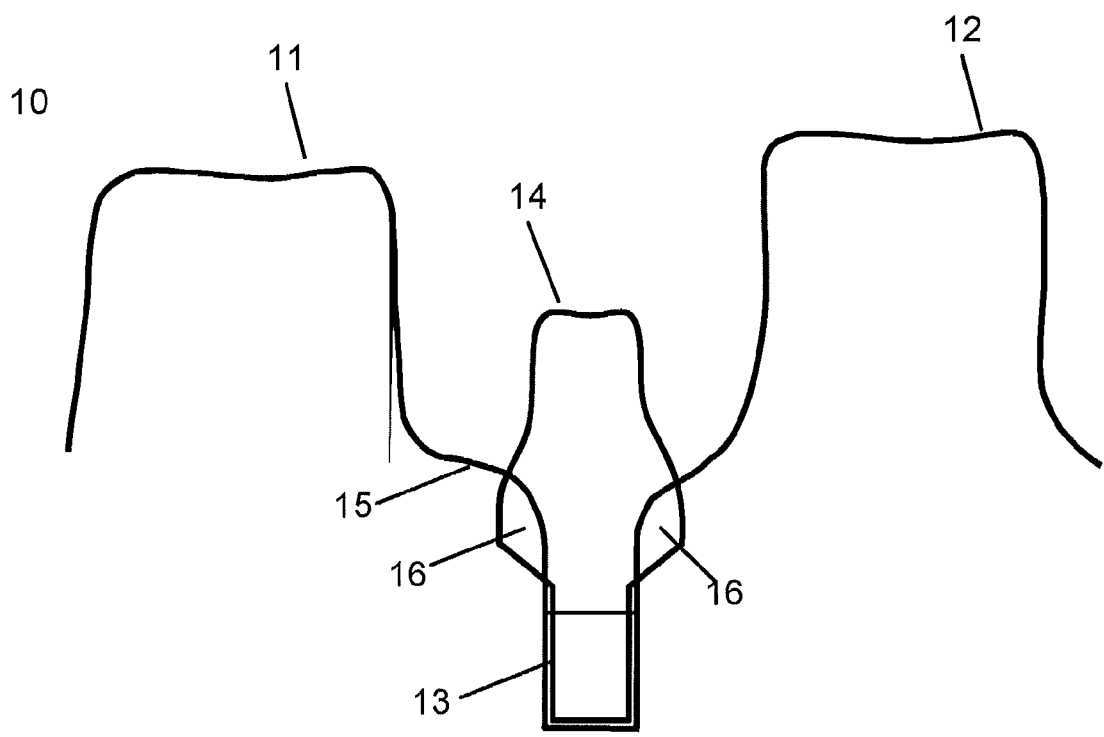
FIG. 1 shows a schematic of a conflict of volumes of a virtual model of a restoration and a gingival part of a virtual model of a set of teeth.

FIG. 1 shows a schematic of a conflict between of volumes of a virtual model of a restoration and a gingival part of a virtual model of a set of teeth.

In procedures relating to a dental implant and a corresponding dental restoration, such as the illustrated abutment, the dental technician often produces a physical model of the set of teeth with an implant analog positioned in the gingival part of the physical model. In some cases, the restoration collides with the gingival part of the physical model of the set of teeth such that the restoration cannot be inserted in the physical model of the set of teeth, i.e. the dental restoration cannot be positioned in the anatomical correct position in the physical model of the set of teeth.

A virtual representation of this situation is illustrated in FIG. 1, where a virtual model 10 of the set of teeth shows two teeth 11, 12 and an implant 13 which in the manufactured physical model is replaced by an implant analog and a first surface 15 of which at least a part relates to the emergence profile of the gingiva. A virtual model of the restoration 14 is inserted in the virtual model 10 of the set of teeth in its anatomical correct position. As seen in the figure, there is an overlap 16 between the volumes of the virtual model of the restoration 14 and the gingival part of the virtual model 10 of the set of teeth. For a restoration and a physical model of the set of teeth the conflict represented by the virtual overlap 16 prevents the insertion of the restoration.

The virtual model of the set of teeth 10 may be generated from one or more three dimensional representations of the set of teeth provided by e.g. scanning an impression of the set of teeth or by direct intra-oral scanning using a handheld scanner, such as the TRIOS™ intra oral-scanner.

The scanning may provide a three dimensional representations in the form of a point cloud which can be converted to a virtual model of the set of teeth by e.g. triangulation.

FIG. 2 shows an embodiment of a method according to the invention, wherein the virtual model of the set of teeth 10 is modified by virtually removing a portion of the gingival part, such that space for a softer material is provided in a physical model manufactured from the modified virtual model of the set of teeth.

Figure 2A:
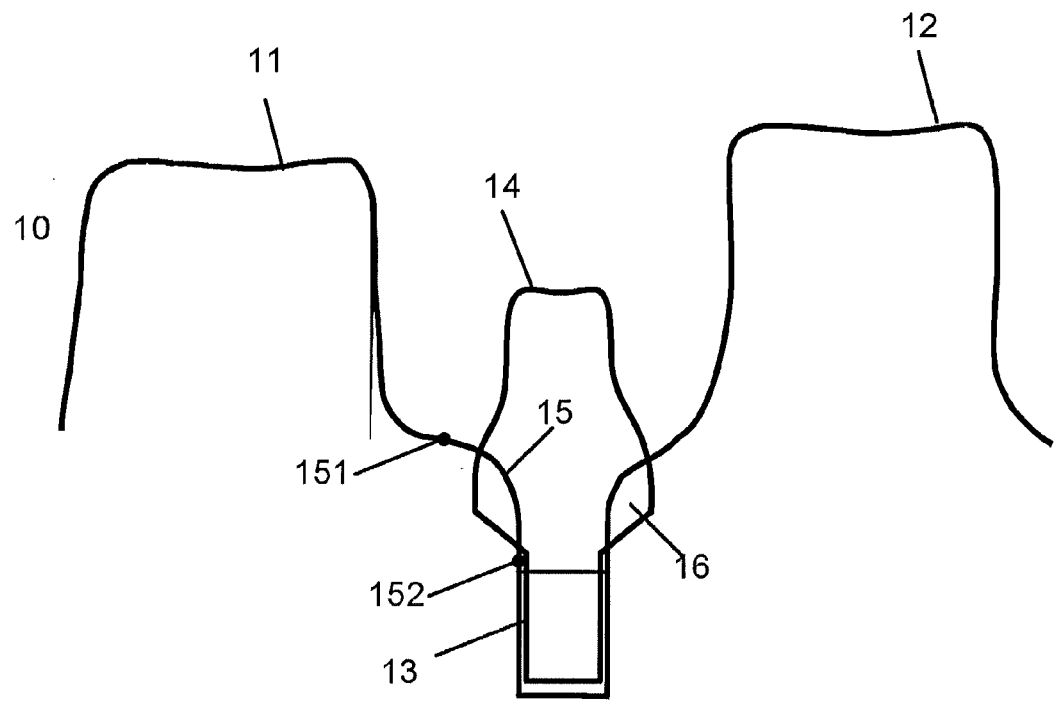
FIG. 2 shows an embodiment of the method according to the invention.

In FIG. 2a, the virtual model 10 of the set of teeth shows two teeth 11, 12 and an implant analog 13. The virtual model of the restoration 14 is virtually inserted such that it is arranged in its anatomical correct position. The overlap 16 prevents the insertion of the restoration in a physical model corresponding to the virtual model 10 of the set of teeth as described above in relation to FIG. 1.

The boundaries of a section which is to be modified can be identified using a first 3D spline 151 and a second 3D spline 152. The 3D splines can be defined manually be an operator using e.g. a pointing tool, such as a computer mouse, and a computer screen onto which the virtual model 10 of the set of teeth is visualized. The boundaries can also be derived automatically using computer implemented algorithms configured for determining e.g. a preparation line of an abutment.

Figure 2B:
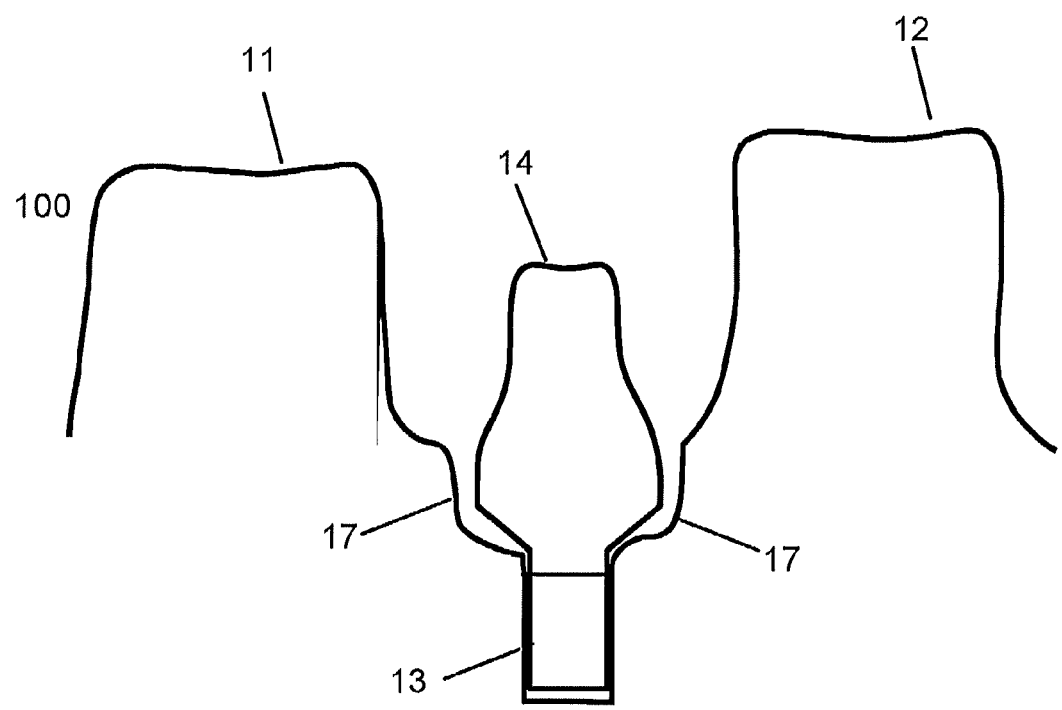

In FIG. 2b, the gingival part of the virtual model 10 of the set of teeth has been modified such that the section now is shaped according to a second surface 17, where the second surface 17 is such that the overlap 16 seen in FIG. 2a is avoided. This corresponds to having virtually removed a portion of the gingival part of the virtual model 10 of the set of teeth, such that it changes from having a shape according to the first surface 15 to a shape according to the second surface 17 in the modified virtual model 100 of the set of teeth.

In the figure, the second surface 17 has a smooth transition from the first to the second 3D spline. The virtually removed portion may be also defined by extending a cylinder to a horizontal plane spanned by the second 3D spline 152, where the cross section of the cylinder is shaped according to the first 3D spline 151.

Figure 2C:
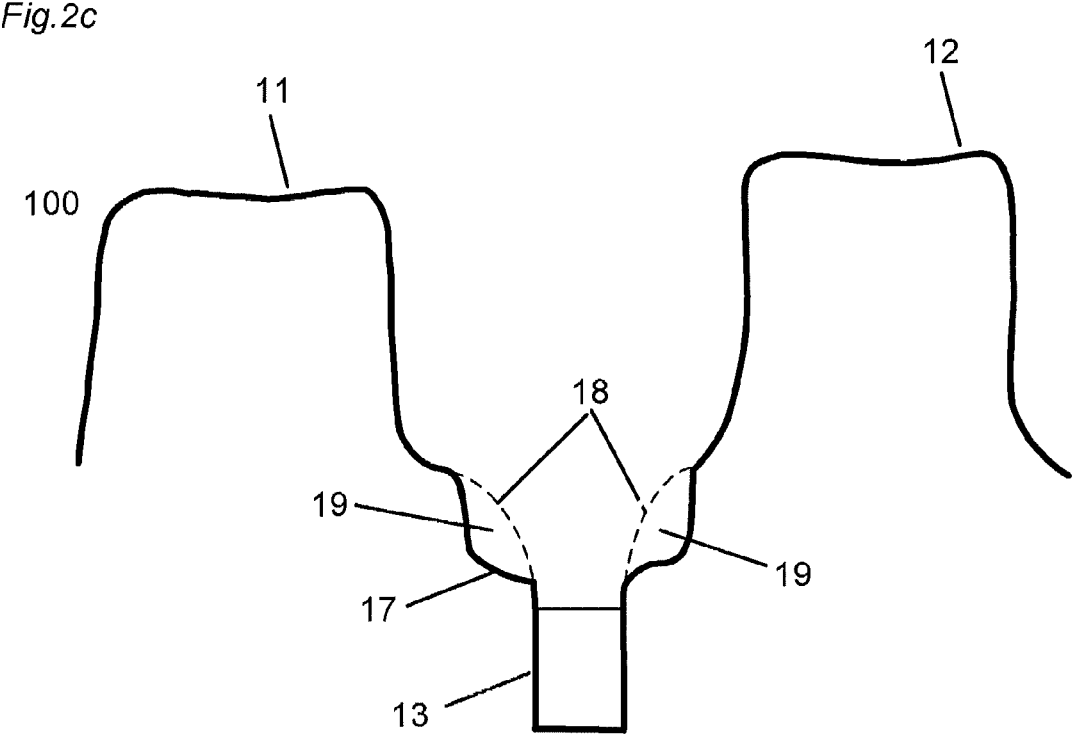

Based on the modified virtual model 100 of the set of teeth, a third surface 18 may be determined digitally e.g. by defining third and fourth 3D splines on the modified virtual model 100. The third and fourth 3D splines are then connected to define the third surface 18. The 3D third and fourth splines may be identical to the first and second 3D splines 151, 152 used for identifying the boundaries of the portion which is virtually removed to make space for the second gingival region 19. I.e. the region 19 is defined defined by the second surface 17 and the third surface 18 as illustrated in FIG. 2c. In a physical model 101 manufactured from the modified virtual model 100 of the set of teeth a relatively soft, compressible material may be provided in the second gingiva region 19. The softer material portion can be manufactured by 3D printing and then arranged at the physical model of the set of teeth 101.

Figure 2D:
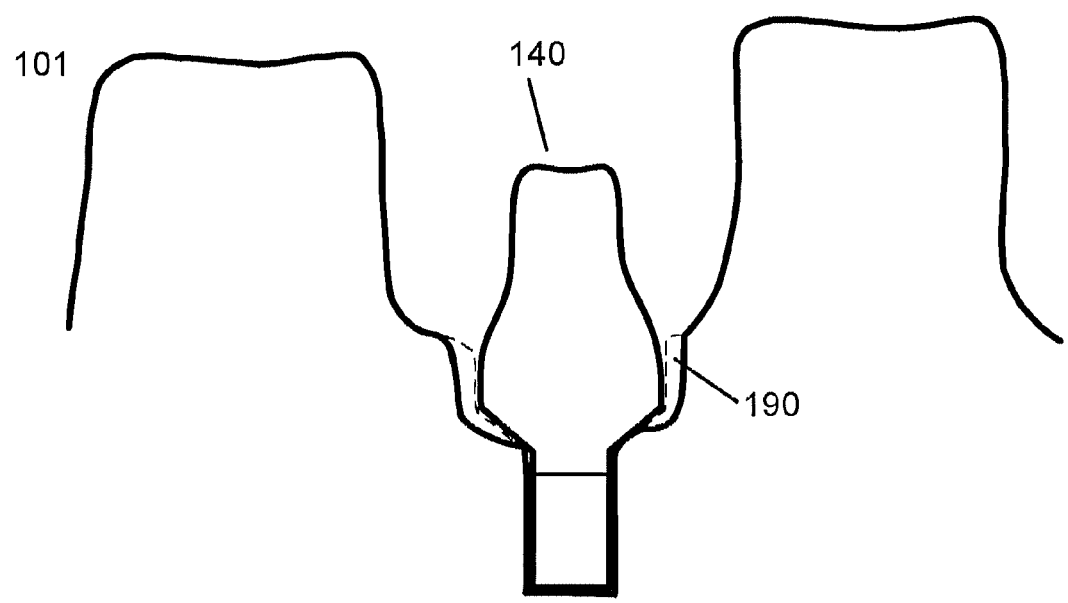

FIG. 2d shows an abutment 140 inserted into the physical model of the set of teeth 101 with a soft, compressible material in the second gingival region 190.

When the second gingival region 19 is shaped according to the third surface 18, there is still an overlap between the volumes of the virtual model of the dental restoration and the gingival part of the modified virtual model 100 of the set of teeth (now having a surface according to the third surface 18), However, when the second material is sufficiently soft and compressible, the second gingival region 190 is deformed when the physical restoration 140 is inserted in the physical model of the set of teeth 100 thus allowing it to be arranged in its anatomically correct position as illustrated in FIG. 2d.

FIG. 3 shows an embodiment of a method according to the invention, wherein the virtual model 10 of the set of teeth is modified by virtually removing a portion of the gingival part.

Figure 3A:
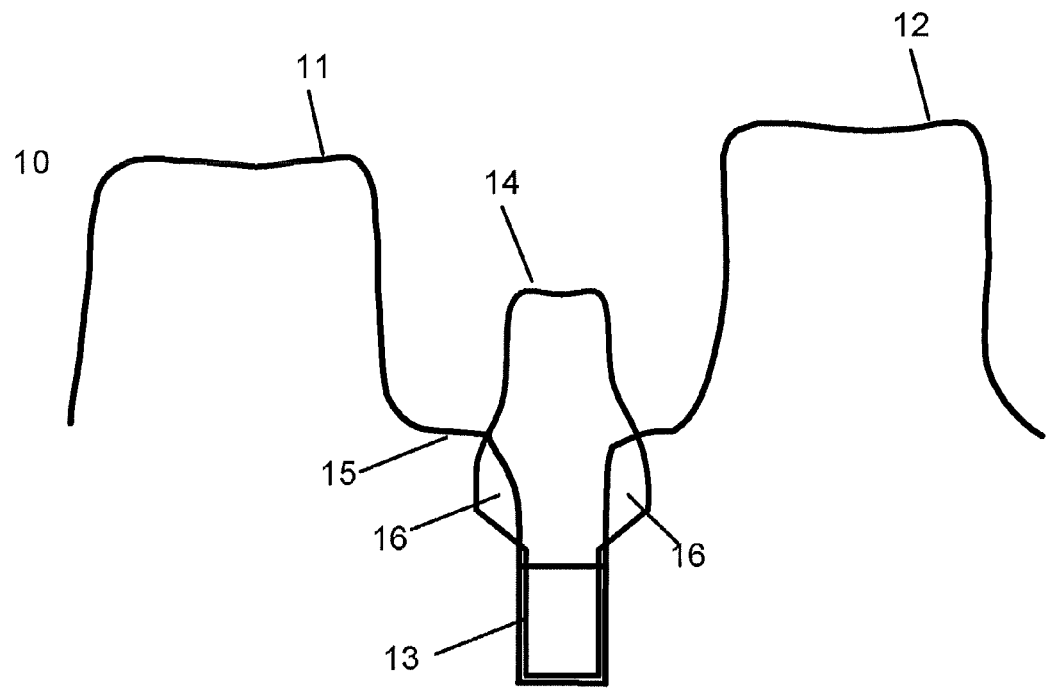
FIG. 3 shows an embodiment of the method according to the invention

In FIG. 3a, the virtual model of the set of teeth 10 shows two teeth 11, 12 and an implant/implant analog 13. The virtual model of the restoration 14 is virtually inserted in its anatomical correct position. The virtual overlap 16 prevents the insertion of the restoration into a physical model corresponding to the virtual model 10 of the set of teeth as described above in relation to FIG. 1.

Figure 3B:
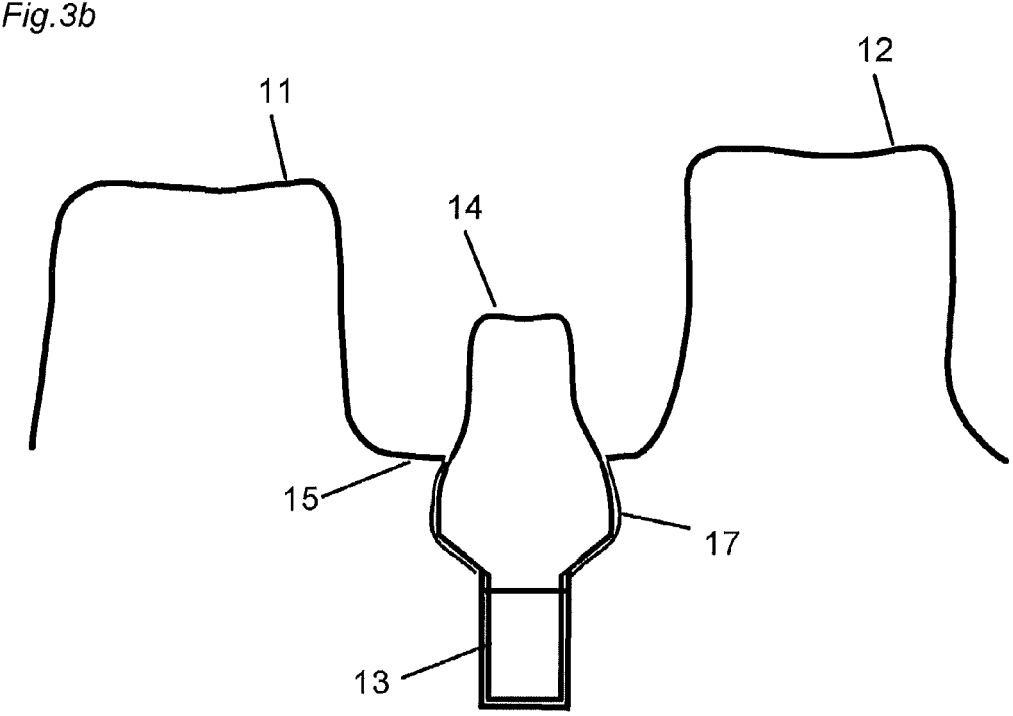

In FIG. 3b, a portion of the gingiva in the region configured for insertion of the restoration has been virtually removed such that the gingiva in the region now defines a second surface 17. The virtual overlap 16 seen in FIG. 3a is now avoided and there is space for the virtual model of the restoration 14 at its anatomically correct position. The second surface 17 can be defined by offsetting the surface of the virtual model of the restoration 14, such as by providing a uniform offset as seen in the figure.

Due to the undercut shape of the second surface 17, it may however not be possible to insert the restoration in a physical model manufactured from the virtual model 10 of the set of teeth illustrated in FIG. 3b.

Figure 3C:
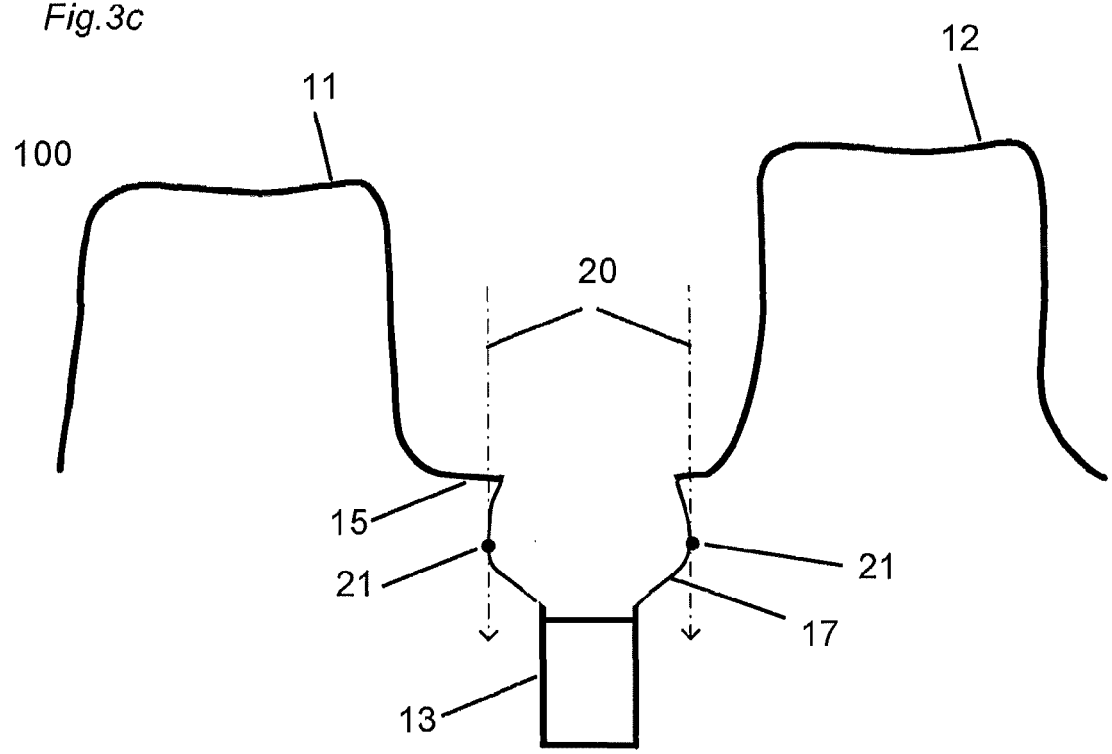
Figure 3D:
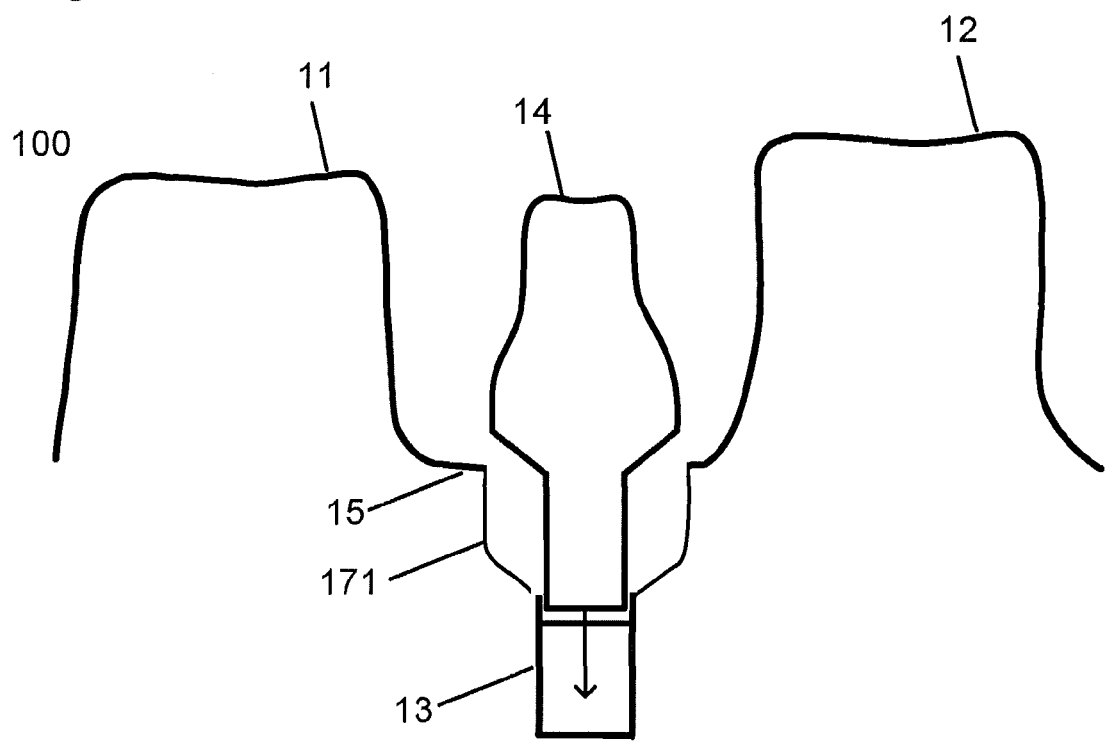

In FIGS. 3c and 3d, the insertion direction 20 for the restoration is taken into account. The insertion direction can be based on the orientation and position of the implant/implant analog 13 in the virtual model 10 of the set of teeth. A circumference line 21 is defined at the outer circumference of the second surface 17 when this is viewed along the insertion direction 20. The circumference line 21 can be determined using computer implemented algorithms.

A cylinder enclosing an extrusion volume can then be defined by the surface generated by translating the circumference line 21 along the insertion path 20 away from the implant analog 13. When the extrusion volume is subtracted from the virtual model 10 of the set of teeth a corrected second surface 171 is provided. Above the circumference line, the corrected second surface 171 differs from the second surface 17 due to said correction.

In a physical model manufactured from the modified virtual model 100 of the set of teeth, the correction with respect to the insertion direction provides that the physical model has no undercuts when viewed along the insertion direction of the restoration, such that the restoration can be inserted into this physical model.

FIG. 4 shows an example of digitally repositioning the the gingiva around a restoration.

Figure 4A:
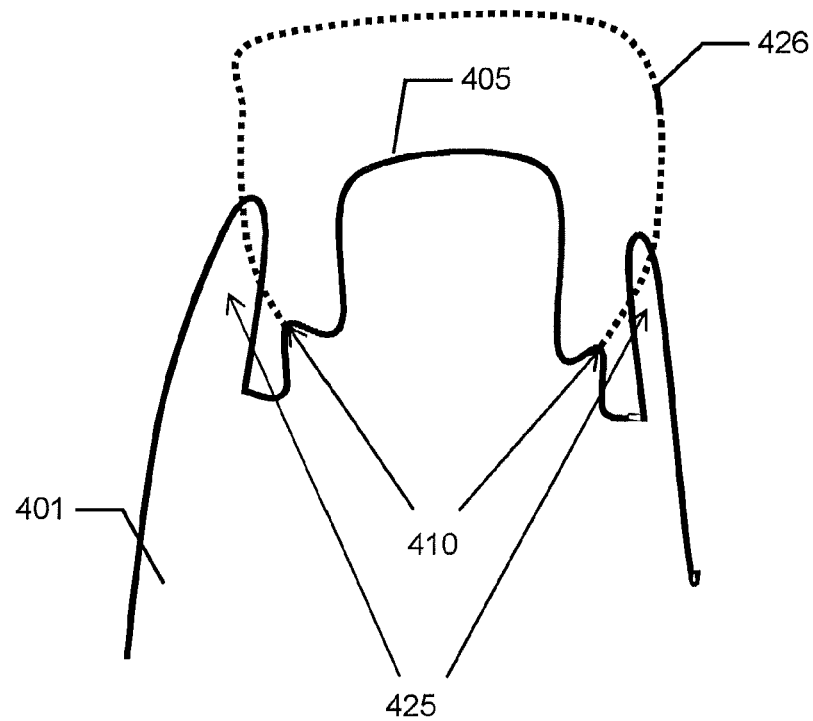
FIG. 4 shows an example of digitally repositioning the gingival part of the model around a restoration.

FIG. 4a) shows the virtual model 401 of the set of teeth before a portion of the gingiva 425 has been digitally repositioned.

Figure 4B:
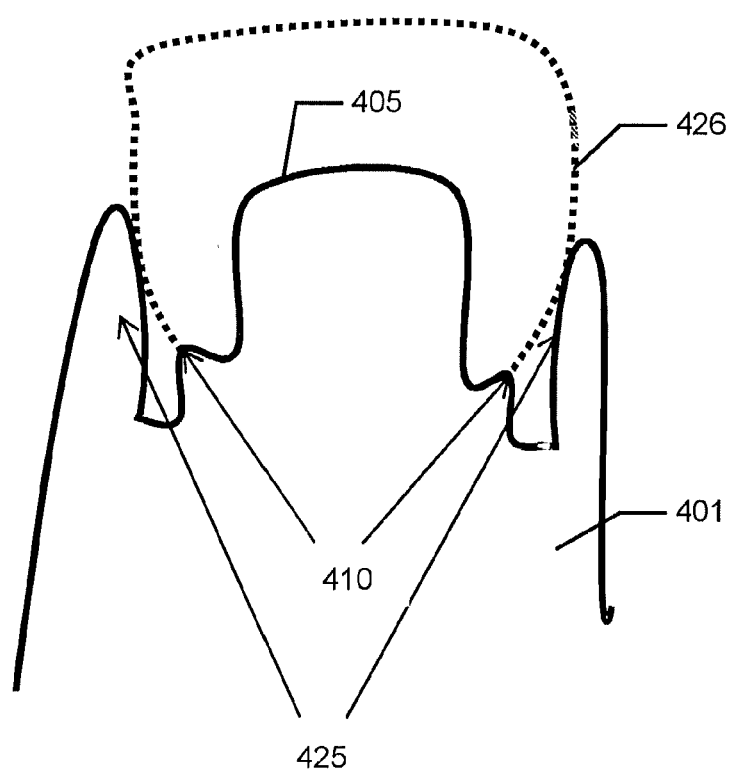

FIG. 4b) shows the virtual model 401 of the set of teeth after a portion of the gingiva 425 has been digitally repositioned. After the gingival part 425 has been moved, the virtual model 401 of the set of teeth can be manufactured.

When a tooth is prepared in the mouth of the patient, so much of the tooth may be grinded away, that the soft, compliant gingival tissue around the prepared tooth will adjoin or follow or collapse to follow the new reduced shape of the prepared tooth instead of remaining in the original shape following the original non-prepared tooth. When digitally repositioning, removing, or relocating the gingival part 425 of the virtual model 401 of the set of teeth around the restoration 405 then there is space for a restoration 426 and veneering.

The gingival part 425 of the virtual model 401 of the set of teeth is moved outwards relative to the restoration 405, i.e. away from the restoration, and it is moved without changing the size of gingival part 425, only the shape of the gingival part 425 is changed.

If the virtual model of the restoration 426 is designed using CAD, it can be derived from the CAD program how much the gingival part 425 on the virtual model 401 of the set of teeth should be moved in order to fit the modeled virtual model of the restoration 426.

Figure 5A:
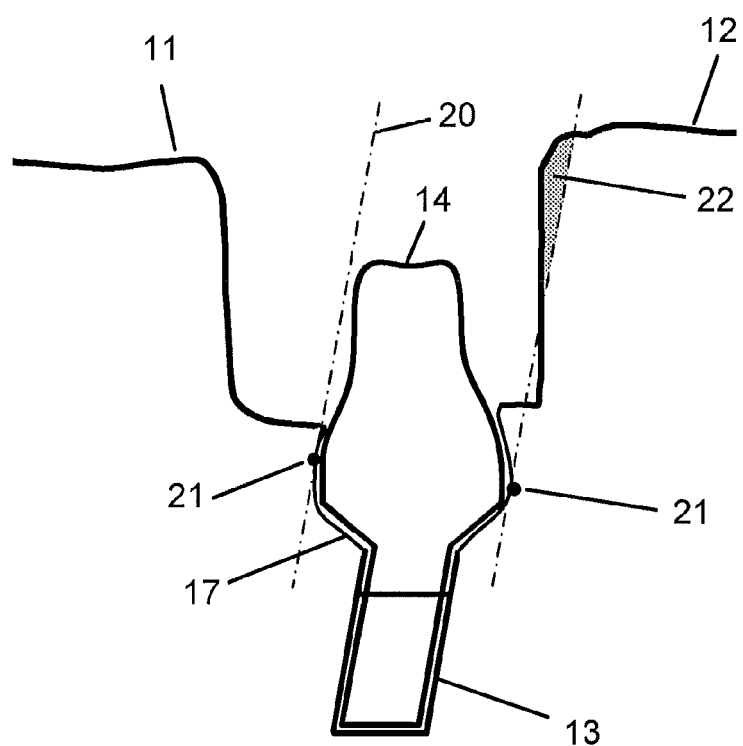
FIG. 5 shows an embodiment of a method according to the invention, wherein collision between an extrusion volume and a teeth portion of the virtual model of the set of teeth is avoided.
Figure 5B:
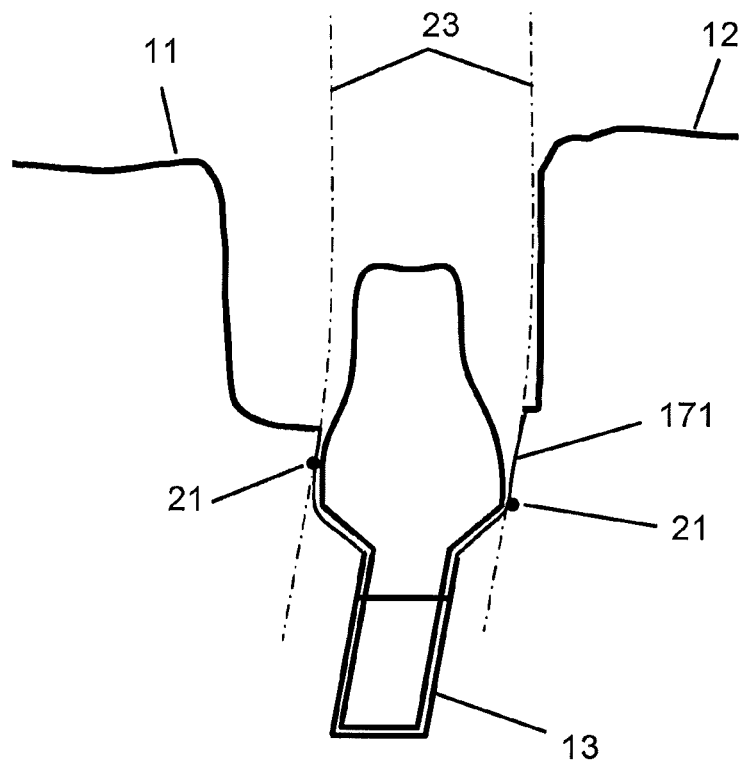

FIG. 5 shows an embodiment of a method according to the invention, wherein collision between an extrusion volume and a teeth portion of the virtual model of the set of teeth is avoided In FIG. 5, the insertion direction 20 for the restoration is taken into account when modifying the gingival part of the virtual model of the set of teeth. A circumference line 21 line is defined at a second surface 17 defined by an offset of the virtual model of the restoration 14. The insertion direction 20 is determined from the orientation and position of the implant analog 13 in the virtual model of the set of teeth. In the example of FIG. 5, the insertion direction 20 is tilted relative to the longitudinal axis of the teeth 11, 12. This causes the extrusion volume (defined by the insertion direction 20 and the circumference line 21) to collide with a tooth portion 22 of the virtual model of the set of teeth. The restoration hence cannot be inserted along the insertion direction 20 into a physical model manufactured from the virtual model of the set of teeth illustrated in FIG. 5a. However, at some distance from the implant region, the restoration may follow a different path such that the collision may be avoided while the path still is aligned with the insertion direction 20 at the implant analog. Such an insertion path 23 is illustrated in FIG. 5b.

The insertion path 23 may be derived by combining a first extrusion volume defined by the circumference line 21 and the insertion direction 20 at the implant analog and a second extrusion volume defined by an upper circumference line and an upper insertion direction, where the upper circumference line may be defined with the corresponding part of the restoration at the incisal edge of the neighboring teeth.

Figure 6:
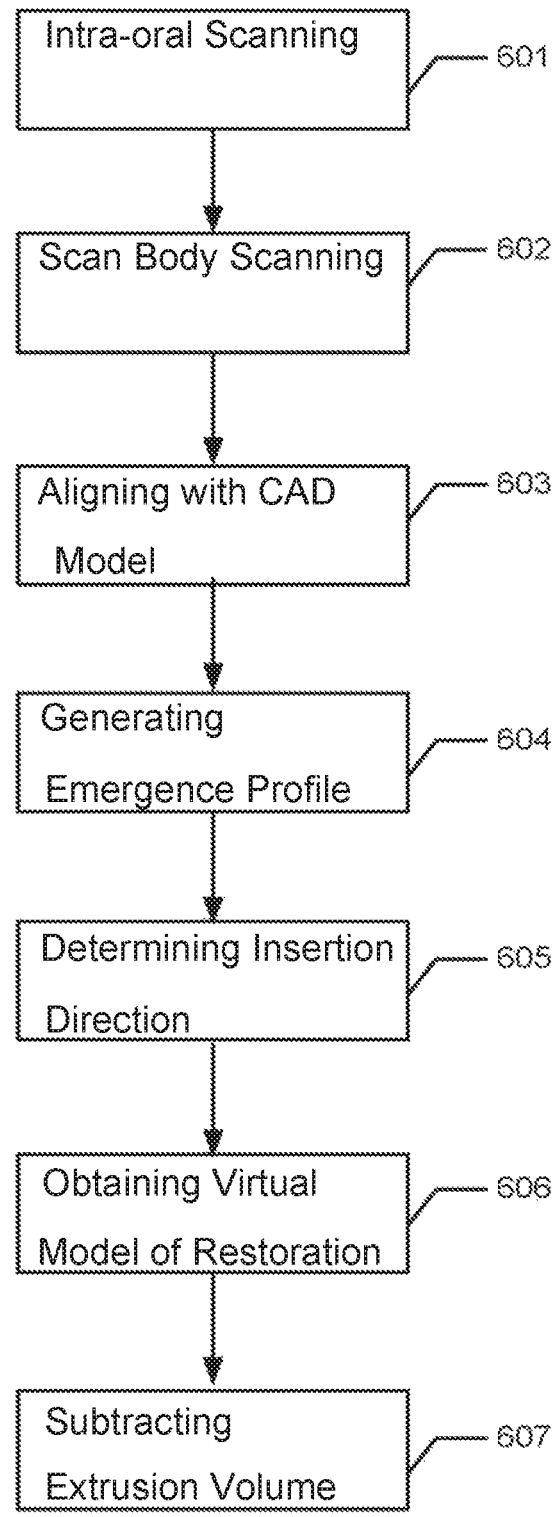
FIG. 6 describes how the virtual model of the set of teeth can be generated and modified

FIG. 6 describes how the virtual model of the set of teeth can be generated and modified to provide that the virtual model of the restoration can be virtually inserted with no overlap between the volume of the restoration and the volume of the gingival part of the virtual model of the set of teeth.

The starting point of this part of the procedure is where an implant is placed in the patient's jaw bone and an operator wishes to design a virtual model of the set of teeth such that a physical model manufactured from the virtual model of the set of teeth allows an abutment to be inserted. When the abutment can be inserted in the physical model of the teeth a crown designed for the patient can be arranged at the abutment and the aestical and functional properties of the designed crown (and abutment) can be evaluated.

A second three dimensional representation of the set of teeth is obtained by intra-oral scanning in 601 and a second virtual model of the set of teeth is generated. A sealing unit may be arranged in the implant during this scanning, but this sealing unit does not cover the emergence profile of the gingiva in the region. A second virtual model of the set of teeth which includes the emergence line of the gingival is then generated.

A scan body is then arranged in the implant and a first three dimensional representation of the set of teeth is obtained in a first scanning 602. The first and the second scanning use a common reference system such that the data of the first three dimensional representation can be directly transferred to the second virtual model of the set of teeth. Data relating to the parts of the set of teeth surrounding the region in which the implant is situated were already obtained in the second scanning so in the first scanning only the region of the implant is scanned With the data from the first scanning transferred to the second virtual model of the set of teeth, this virtual model now comprises both data relating to the emergence profile and to the scan body.

A CAD model of the scan body is then aligned 603 with the scan body portion of this second virtual model. Thereby the position and orientation of the implant can be derived and a virtual model with the implant position and orientation and with the emergence profile is generated 604.

The order at which these two scans are obtained is not important, such that the first scanning can be performed before the second. If the scan with the scan body is made initially, the scan body is removed from the implant before the scanning without the scan body is made. The emergence profile can then be extracted from the second virtual model (or directly from the second three dimensional representation of the set of teeth) and transferred to the first virtual model, such that a virtual model of the set of teeth is generated.

In both cases, the generated virtual model of the set of teeth comprises a gingival part of the set of teeth, said gingival part comprising a region configured for insertion of a restoration with both the emergence profile of the gingival and the implant position and orientation.

The first and second scanning can also be of impressions of the patient's set of teeth using a scan flag to indicate the position and orientation of the implant.

The antagonist may also be scanned such that the occlusion of the restoration can be evaluated and taken into account when modelling e.g a crown for the implant.

The insertion direction of the restoration is determined in step 605.

A virtual model of the restoration for the set of teeth, such as a virtual model of an abutment, is obtained in step 606 and virtually aligned with the generated virtual model of the set of teeth. The virtual model of the restoration may be designed to the patient's set of teeth by e.g. defining the margin line using a 3D spline.

When a final design of the restoration is obtained, it is subtracted from the virtual model of the set of teeth, or a volume corresponding to an offset surface of the virtual model of the restoration is subtracted from the virtual model of the set of teeth. An extrusion volume can then be determined based on a circumference line of the restoration and the insertion direction. The extrusion volume is then subtracted from the virtual model of the set of teeth such that the modified virtual model of the set of teeth is provided 607.

The generated and modified virtual model of the set of teeth is then such that the virtual model of the dental restoration can be virtually inserted in said region with no overlap between the volume of the restoration and the volume of the gingival part. A result of this procedure is that a restoration manufactured from the virtual model of the of the restoration, such as an abutment, can be inserted into a physical model of the set of teeth manufactured from said modified virtual model of the set of teeth.

Figure 7A:
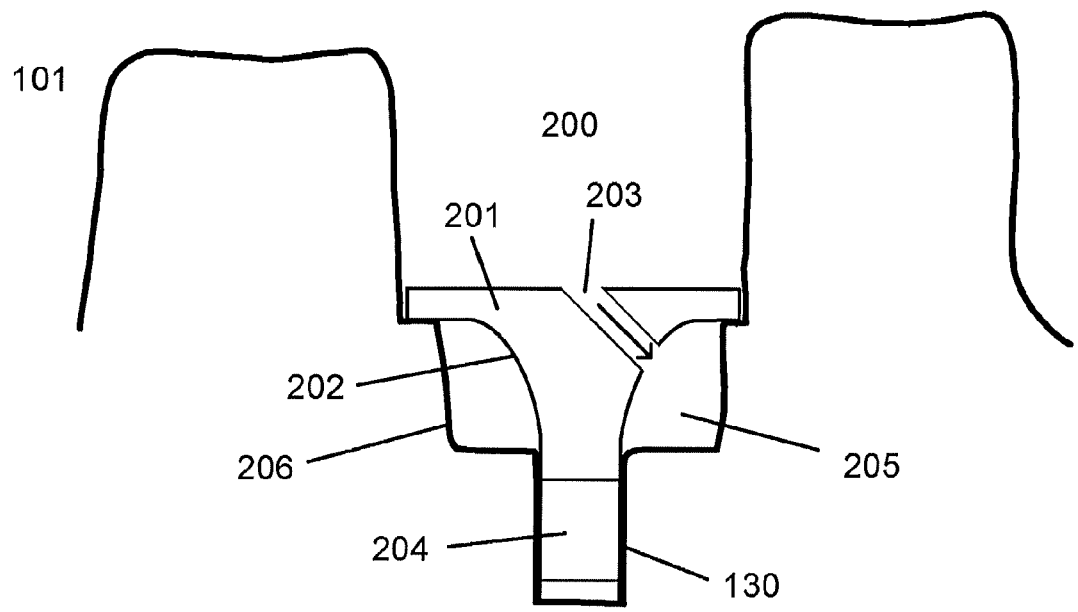
FIG. 7 shows how a cover arranged in relation to a physical model of the teeth can be used when realizing a second gingival region made of a relatively soft and compressible material.

FIG. 7 shows how a cover arranged in relation to a physical model of the teeth can be used when realizing a second gingival region made of a relatively soft and compressible material.

The cover 200 comprises a top portion 201 having a model facing surface 202 and a through channel 203. Further the cover 200 has an implant engaging portion 204, which is configured to fit into the implant analog 130 of a physical model of a set of teeth 101. When the cover 200 is arranged in relation to the implant analog 130, the model facing surface 202 encloses a volume 205 in collaboration with an opposing surface 206 of the physical model. The through channel 203 provides a liquid connection to the enclosed volume 205, such that the enclosed volume can be filled with a second gingival material via the though channel 203. When the enclosed volume 205 is filled with the second gingival material, the second gingival material is shaped according to the model facing surface 202.

Figure 7B:
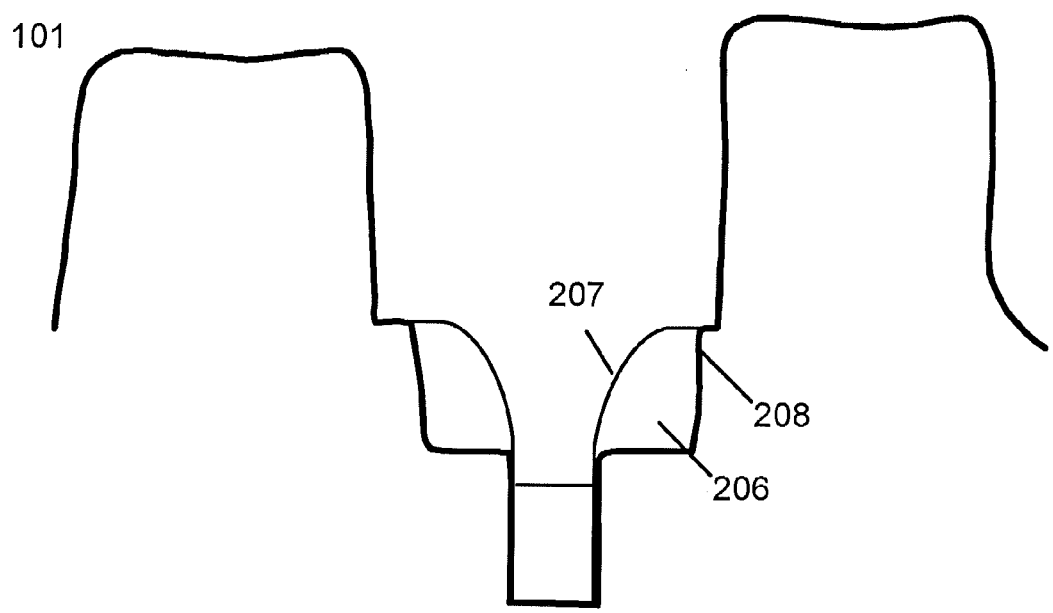

When the cover is removed the second gingival region 206 (corresponding to the enclosed volume 205) filled with the second gingival material has been formed at the physical model of the set of teeth 101 as illustrated in FIG. 7b. The surface 207 of the second gingival region 206 is shaped according to the model facing surface 202 of the cover.

The surface 208 of the physical model 101 of the set of teeth can be defined manually by grinding.

Figure 7C:
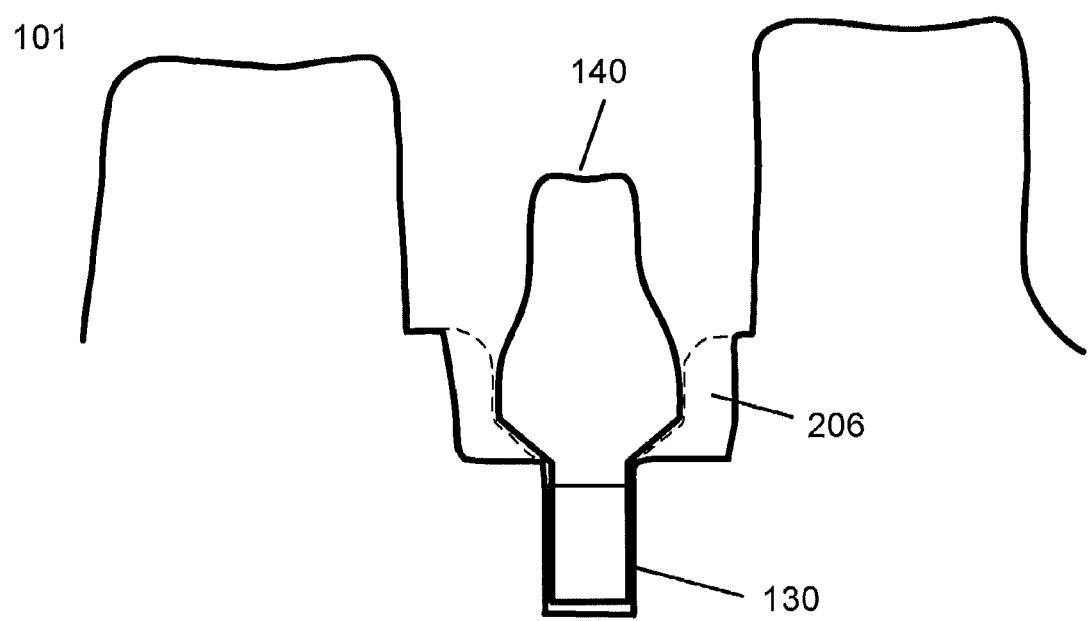

If the second gingival material is sufficiently soft and compressible, the dental restoration, here exemplified by the abutment 140, can be inserted into the implant analog 130 be applying a pressure which deforms the second gingival material enough to allow the insertion as illustrated in FIG. 7c. The second material can for example be a dental silicone.

In some embodiments, model facing surface of the cover is shaped according to the surface of a known abutment. I.e. different covers can be manufactured based on the surfaces of known abutments, such that the second gingival section formed by one cover is shaped according to a corresponding abutment. The requirements to the compressability of the second gingival material is then less strict and a larger variety of materials can be used.

FIG. 8 show schematic presentations of the inventive covers according to the present invention.

Figure 8A:
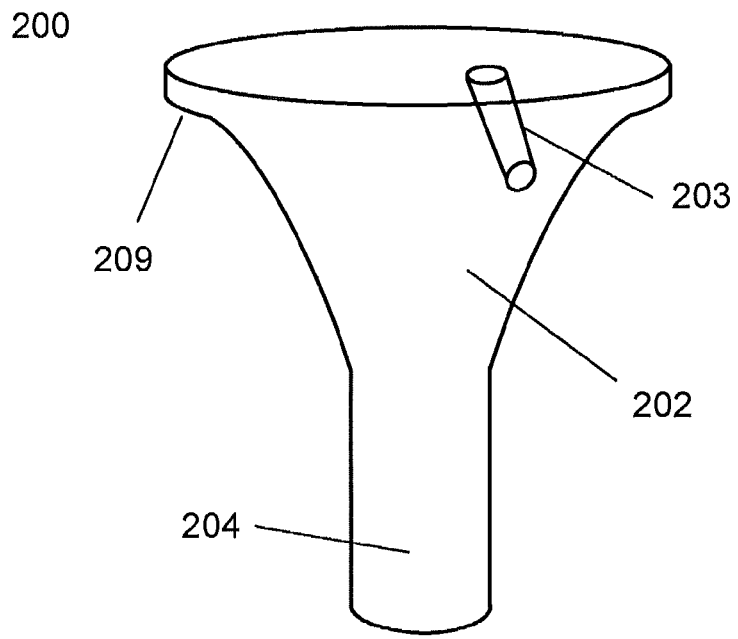
FIG. 8 show schematic presentations of the inventive covers according to the present invention

FIG. 8a. shows an example of a cover 200 with an implant engaging portion 204, and a top portion with a model facing surface 202 and a through passage. When the cover is arranged relative to a physical model of a set of teeth, the implant engaging portion 204 is placed in the implant analog and the lower part 209 of the top portion rests on a gingival part of the physical model. The length of the implant engaging portion 204 is adapted to provide that its position in the implant analog can be adjusted such that the lower part 209 encloses a volume in collaboration with the physical model.

Figure 8B:
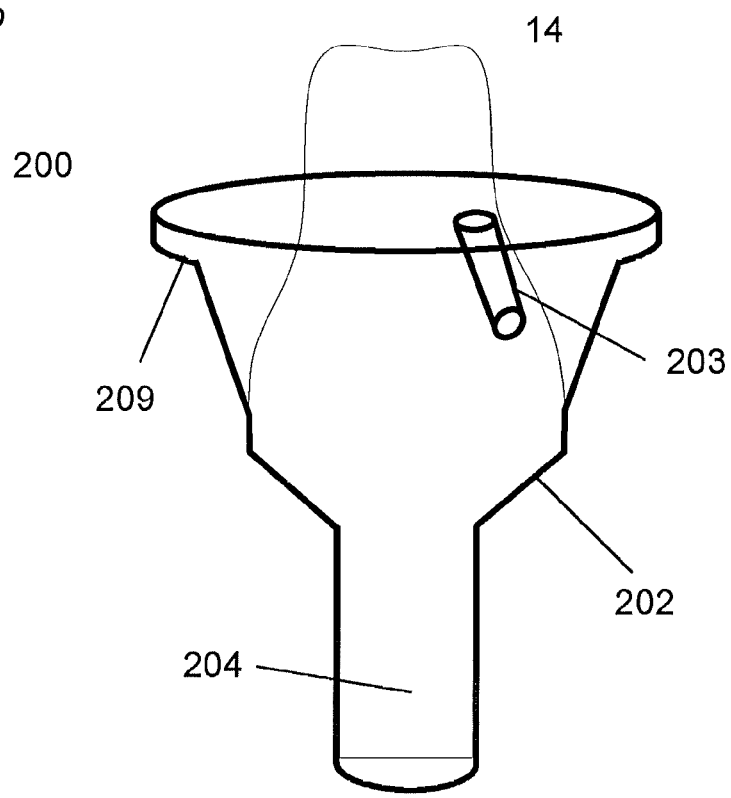

FIG. 8b. shows an example of a cover 200 where the model facing surface 202 is shaped according to the surface of a known abutment 14. The portion of the model facing surface 202 nearest to the implant engaging portion 204 is shaped according to the corresponding surface of the abutment 14 or by a well defined offset of the corresponding surface. When the second gingival region is formed using this cover, the corresponding abutment will fit into the physical model even if the second gingival material is relatively incompressible.

Figure 9:
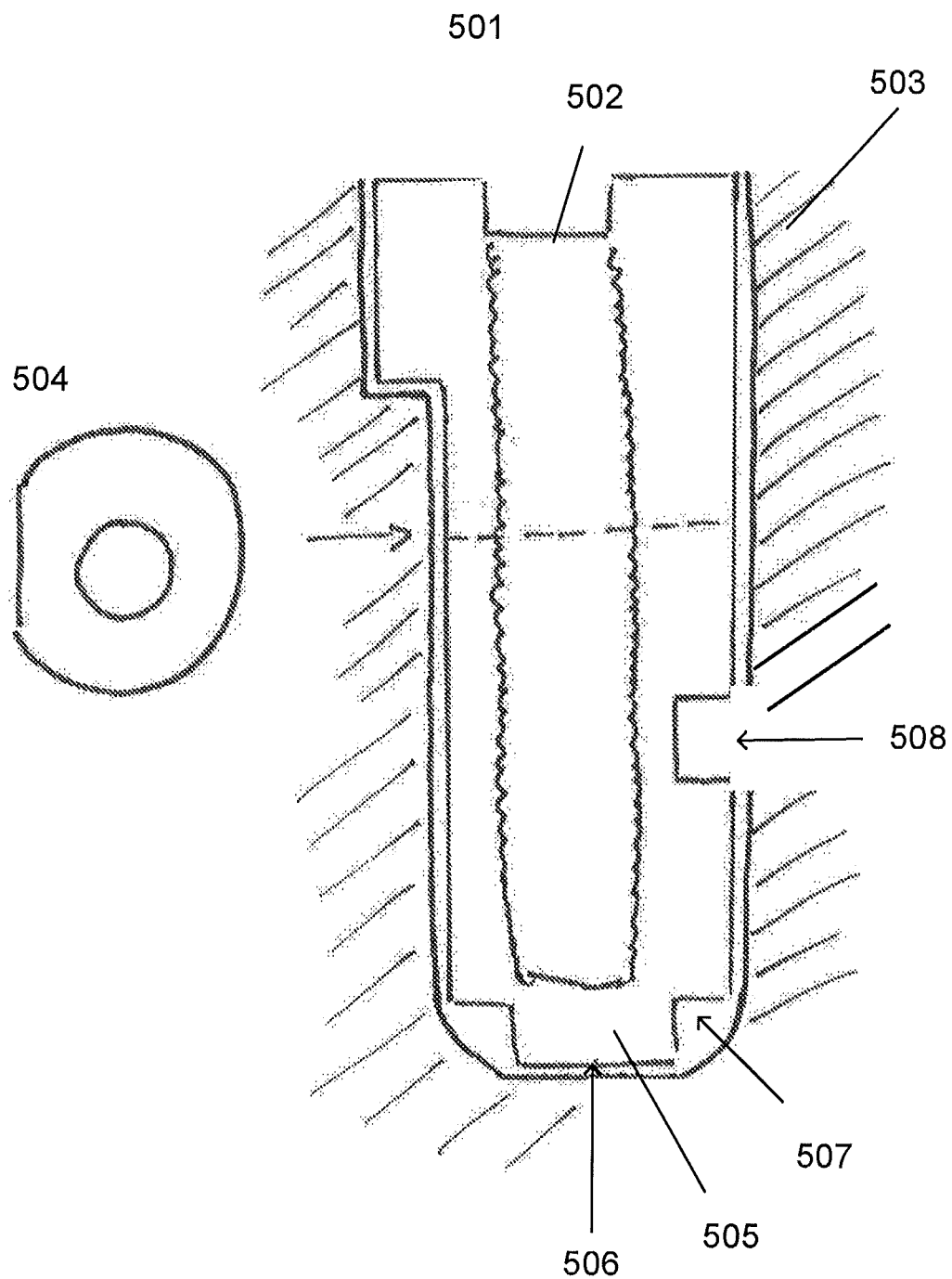
FIG. 9 shows an inventive implant analog.

FIG. 9 shows an example of an implant analog configured to be arranged in the gingival part of a physical model of a set of teeth.

The figure shows a side view of an implant analog 501 arranged in a hole defined in the gingival part 503 of the physical model. A central 502 volume extends along the longitudinal direction of the implant analog from a crown end towards its distal end 505. At the distal end 505, a stop surface 506 is configured to have a reduced cross sectional area such that room is left for rounded corners 507 of the wall of the hole and potentially for excess material that was not removed from the hole. The rounded corners may be generated when the drill used to defined the hole has a rounded tip. The cross sectional shape 504 of the implant analog illustrates one way to ensure that the implant analog can only be arranged with its correct orientation relative to the gingival part of the physical model.

A height inspection groove 508 is defined in the implant analog 501 to allow for visual or a contact based inspection of whether the implant analog 501 is arranged in the correct position in the gingival part of the physical model. A window or a through hole (not illustrated in the Figure) may be provided in the gingival part of the model to allow visual and/or physical contact to the inplant analog from the outside of the model.

The window or through hole may be provided in the virtual modelling of the gingival part of a set of teeth such that it is formed directly with the manufacture of the physical model or after the manufacturing of the physical model.

Figure 10:
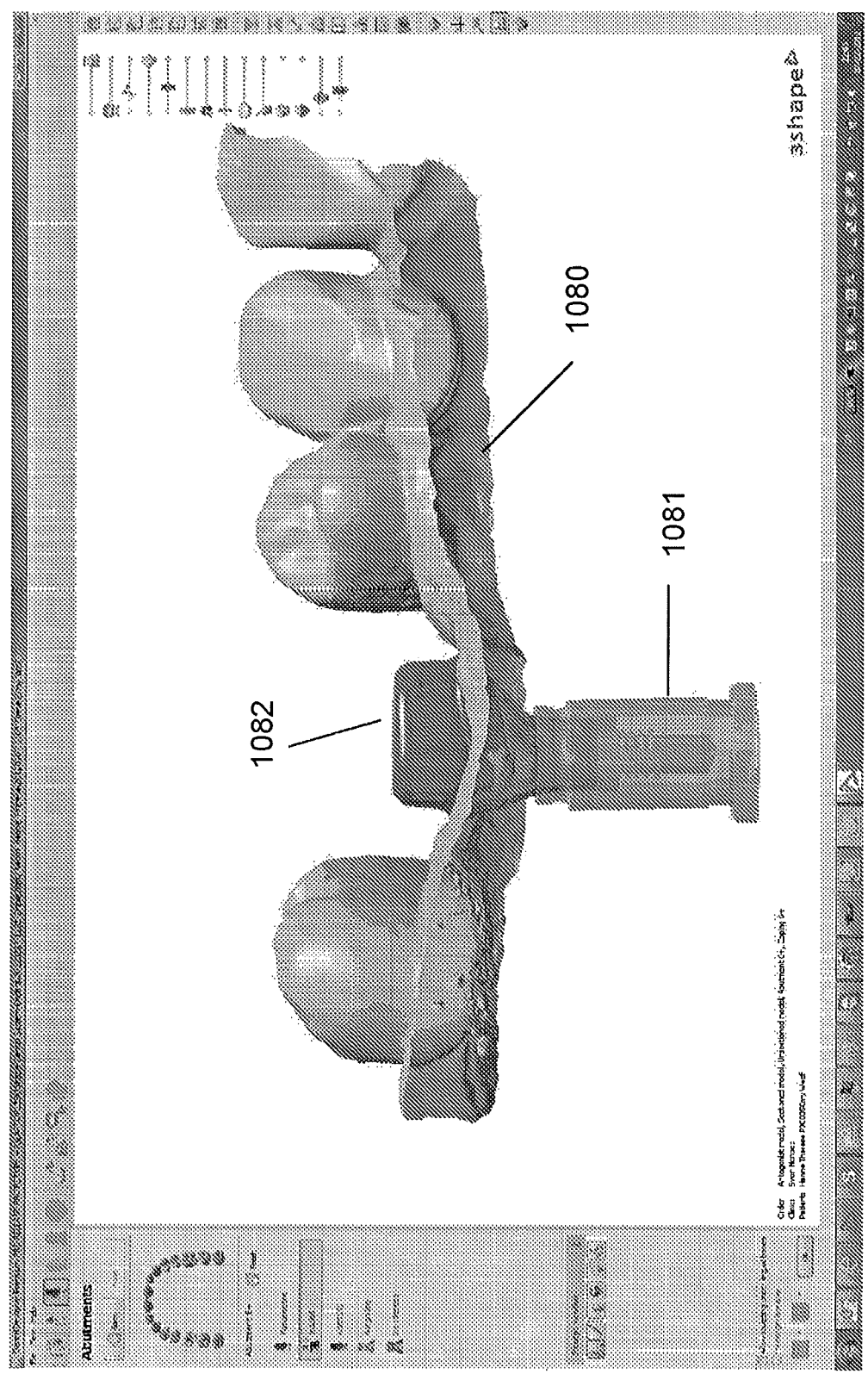
FIGS. 10 and 11 show screen shots from an implementation of the invention.

FIG. 10 show a screen shot from an implementation of the invention

A virtual model 1080 of the set of teeth with the implant 1081 position and orientation has been generated using the method of the invention. Also seen in the screen shot is the restoration 1082 (an abutment) which is to be designed based on the set of teeth.

FIG. 6 described some embodiments of the method for generation such a the virtual model of the set of teeth.

FIG. 11 show screen shots from an implementation of the invention.

Figure 11A:
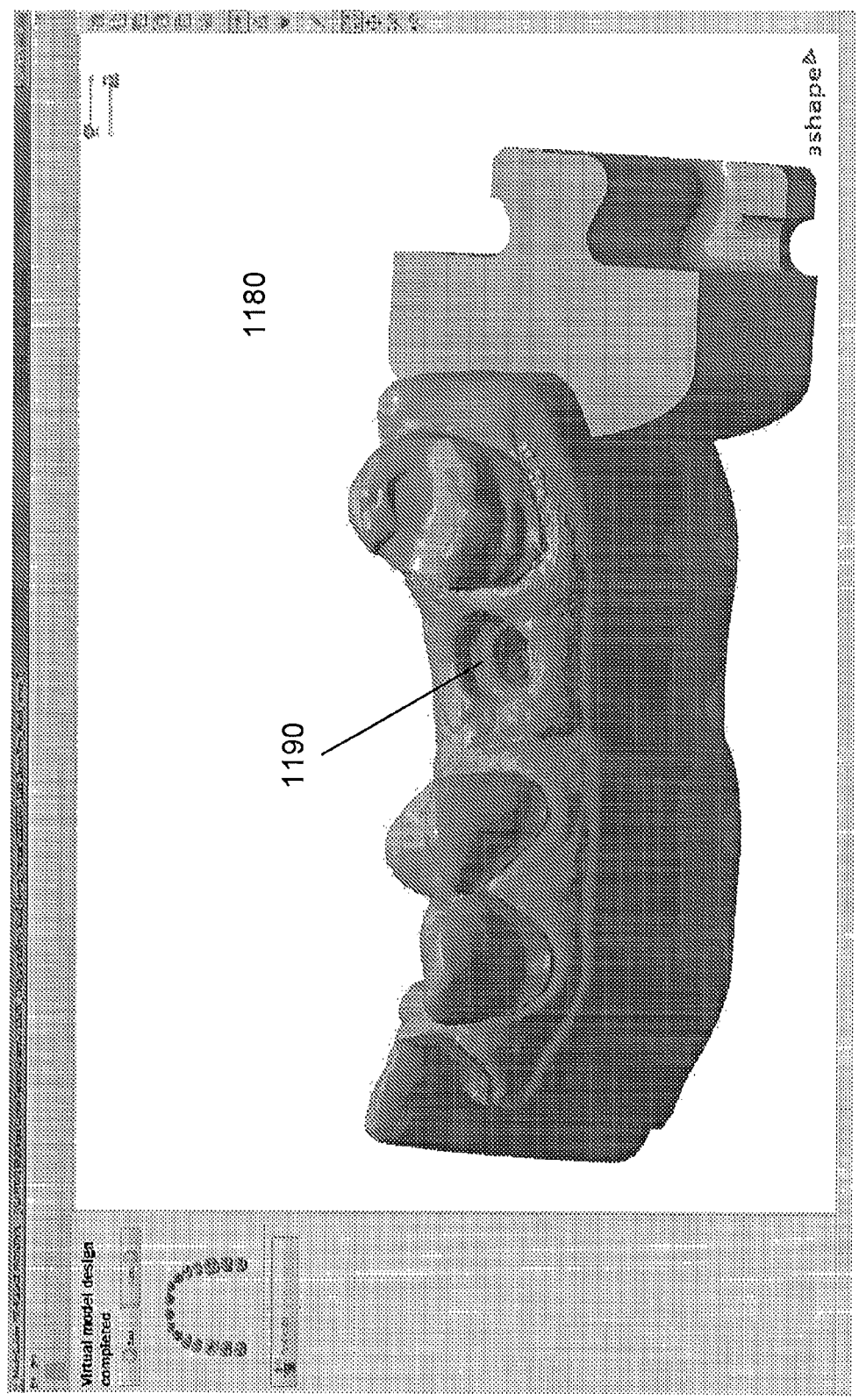
Figure 11B:
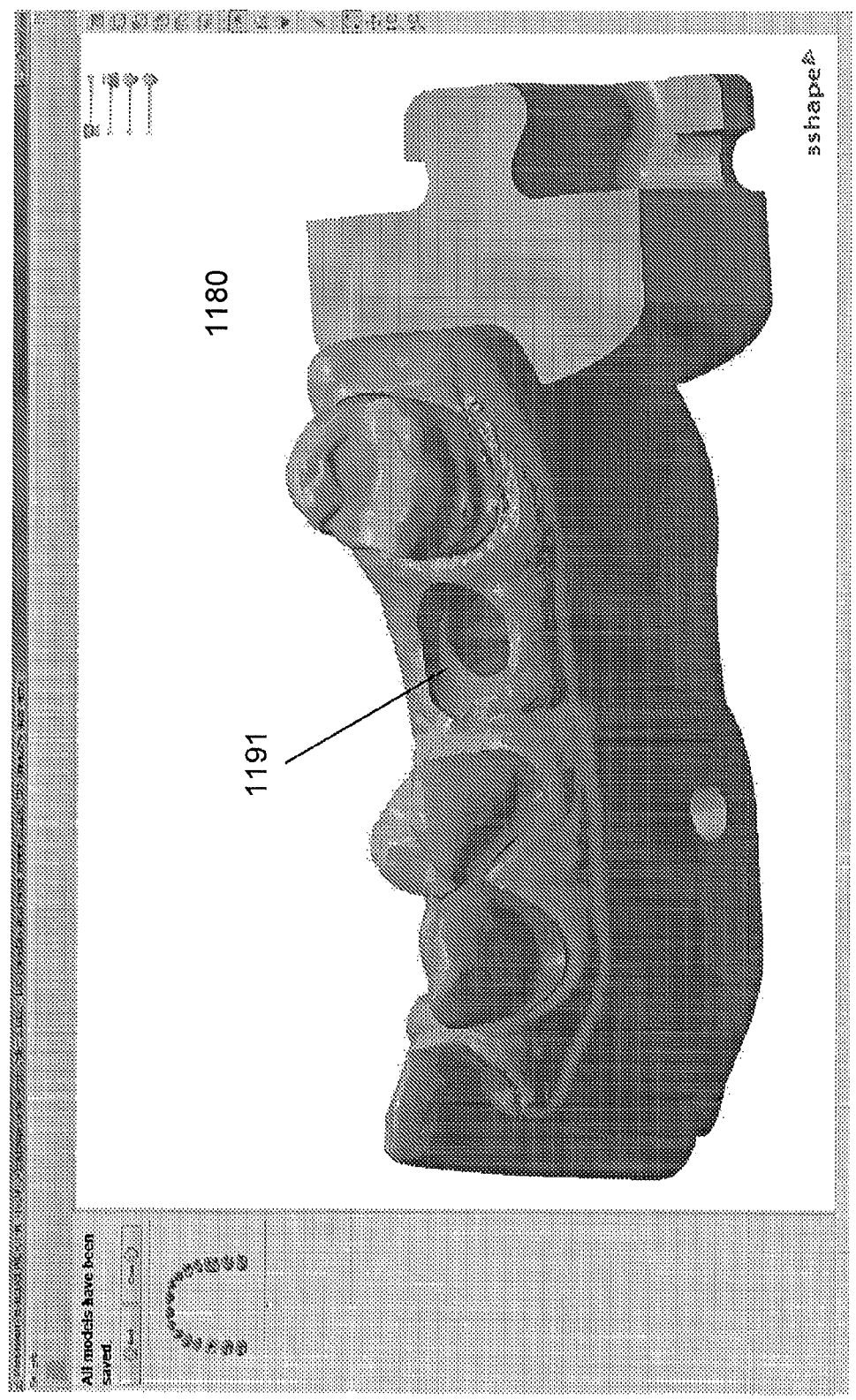

The virtual model of the set of teeth 1180 has now been equipped with a base and connectors for e.g. arranging the manufactured physical model in an articulator. In FIG. 11a the emergence profile 1190 is seen in the region configured for the restoration. In FIG. 11b, the virtual model of the set of teeth has been modified to provide that there is no overlap between the virtual model of the restoration (the abutment) and the virtual of the set of teeth, such that the manufactured restoration can be inserted in a physical model of the set of teeth manufactured from said generated and modified virtual model of the set of teeth.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

It should be emphasized that the term "according to any of the preceding claims" may be interpreted as meaning "according to any one or more of the preceding claims", such that the limitations of one or several dependent claims may be read into an independent claim.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

Items:

1. A method of generating and modifying a virtual model of a set of teeth, said set of teeth comprising a region configured for insertion of a restoration, the region being located in a gingival part of the set of teeth, where the method comprises:

obtaining at least one three dimensional representation of the set of teeth;

generating a virtual model of the set of teeth from said three dimensional representation, where the virtual model of the set of teeth comprises a gingival part, said gingival part comprising a virtual region corresponding to said region configured for insertion of a restoration and at least part of the gingiva surrounding said region;

obtaining a virtual model of said restoration; and modifying the gingival part of the virtual model of the set of teeth such that the virtual model of the restoration can be virtually inserted into said virtual region with no overlap between the volume of said virtual model of the restoration and the volume of said gingival part of the virtual model of the set of teeth.

2. The method according to item 1, wherein a first three dimensional representation of the set of teeth is obtained by scanning the patient's set of teeth with a scan body arranged in said implant region.

3. The method according to item 1 or 2, where said virtual model of the set of teeth is generated at least in part from said first three dimensional representation.

4. The method according to any of the preceding items, wherein a second three dimensional representation of the set of teeth is obtained by scanning the patient's set of teeth with the emergence profile at said implant region being visible.

5. The method according to any of the preceding items, where said virtual model of the set of teeth is generated at least in part from said second three dimensional representation.

6. The method according to any of the preceding items, wherein one of said first or second three dimensional representation of the set of teeth is obtained by scanning a relatively larger section of the patient's set of teeth, and the other of said first or second three dimensional representation then is obtained by scanning a relatively smaller section around the implant region.

7. The method according to any of the preceding items, wherein the method comprises generating a first virtual model of the set of teeth from said first three dimensional representation of the set of teeth.

8. The method according to any of the preceding items, wherein the method comprises generating a second virtual model of the set of teeth from said second three dimensional representation of the set of teeth.

9. The method according to any of the preceding items, wherein the method comprises combining the first and second virtual models of the set of teeth to generate said virtual model of the set of teeth.

10. The method according to any of the preceding items, wherein a virtual model of the scan body is provided and virtually aligned with the first virtual model of the set of teeth to determine the orientation and position of the implant.

11. The method according to any of the preceding items, where the restoration is designed based on the virtual model of the set of teeth.

12. The method according to any of the preceding items, where the restoration is a pre-manufactured restoration such as a pre-manufactured abutment.

13. The method according to any of the preceding items, where modified virtual model of the set of teeth is for manufacturing a physical model of the set of teeth.

14. The method according to any of the preceding items, where at least a sub-gingival part of the virtual model of the restoration is configured to have the shape of an anatomically correct restoration.

15. The method according to any of the preceding items, where the gingival part of the generated virtual model of the set of teeth directly provides that the volume of the restoration and the volume of the gingival part do not overlap.

16. The method according to any of the preceding items, where the virtual model of the set of teeth is generated in one step and where the gingival part of the virtual model subsequently is modified to provide that the volume of the restoration and the volume of the gingival part do not overlap.

17. The method according to any of the preceding items, wherein the gingival part of the virtual model of the set of teeth is modified to provide that the adjoining surfaces of the virtual model of the restoration and the gingival part of the virtual model of the set of teeth follows each other.

18. The method according to any of the preceding items, wherein an offset is provided between the adjoining surfaces of the virtual model of the restoration and the gingival part of the virtual model of the set of teeth.

19. The method according to any of the preceding items, wherein the method comprises determining in insertion path for the restoration.

20. The method according to any of the preceding items, wherein the insertion path is according to the insertion direction at the implant.

21. The method according to any of the preceding items, wherein the method comprises identifying a circumference line for the restoration.

22. The method according to any of the preceding items, wherein the circumference line is defined as the outer circumference of the restoration when the virtual model of the restoration is viewed along the insertion direction.

23. The method according to any of the preceding items, wherein the circumference line is defined as the outer circumference of the offset surface when the offset surface is viewed along the insertion direction.

24. The method according to any of the preceding items, wherein an extrusion volume is defined by the insertion direction and the circumference line.

25. The method according to any of the preceding items, wherein an extrusion volume is defined by the insertion path and the circumference line.

26. The method according to any of the preceding items, wherein modifying the gingival part of the virtual model of the set of teeth comprises digitally cutting a portion of the gingiva away such that the volume of the restoration and the volume of the gingiva do not overlap.

27. A method of generating and modifying a virtual model of a set of teeth for manufacturing a physical model of the set of teeth, where the method comprises:
   obtaining a three dimensional representation of the set of teeth;
   generating a virtual model of the set of teeth from said three dimensional representation, the virtual model of the set of teeth comprising a gingival part comprising a gingiva; and
   modifying the gingival part to enable an insertion of a restoration in a region of the virtual model configured for insertion of a restoration.

28. The method according to any of the preceding items, wherein modifying the gingival part comprises modifying the gingival part of the virtual model generated from the three dimensional representation.

29. The method according to any of the preceding items, wherein modifying the gingival part comprises configuring the material of the gingival part at the restoration to be sufficiently soft such that a restoration may deform the gingival part.

30. The method according to any of the preceding items, wherein modifying the gingival part comprises virtually removing a portion of said gingival part in the region configured for insertion of a restoration.

31. The method according to any of the previous items, wherein the method comprises virtually adding material to the gingival part of the virtual model in the region configured for insertion of a restoration.

32. The method according to any of the preceding items, wherein the method comprises digitally repositioning the gingival part of the model around the restoration, before manufacturing the model.

33. The method according to any of the preceding items, wherein digitally repositioning the gingival part of the virtual model of the set of teeth comprises digitally moving gingiva away from the virtual model of the restoration.

34. The method according to any of the previous items, wherein the gingival part of the virtual model of the set of teeth defines a first surface at the region configured for insertion of a restoration.

35. The method according to any of the preceding items, wherein the first surface follows at least a section of said emergence profile.

36. The method according to any of the preceding items, wherein modifying the virtual model of the set of teeth comprises replacing said first surface by a second surface, where said second surface is shaped such that the virtual model of said restoration can be virtually arranged in said virtual implant region with no overlap with the modified virtual model of the set of teeth.

37. The method according to any of the previous items, wherein the gingival part of the virtual model of the set of teeth after the virtual removal of a portion of the gingiva defines the second surface at the region configured for insertion of a restoration.

38. The method according to any of the preceding items, wherein at least a section of said second surface is defined by offsetting part of the surface of the virtual model of the restoration.

39. The method according to any of the preceding items, wherein the method comprises subtracting the virtual model of the restoration or the volume enclosed by the offset surface from the virtual model of the set of teeth.

40. The method according to any of the previous items, wherein the gingival part of the virtual model of the set of teeth after virtually adding material to the gingiva defines a third surface at the region configured for insertion of a restoration.

41. The method according to any of the previous items, wherein the gingival part of the virtual model of the set of teeth is divided into a first and a second gingival region by the second surface 42. The method according to any of the previous items, where said second gingival region is arranged between the second surface and the third surface, the second surface forming an interface between the first and the second gingival region.

43. The method according to any of the previous items, wherein said third surface is substantially identical to said first surface.

44. The method according to any of the previous items, wherein said first gingival region is configured to be manufactured in a first material in a physical model manufactured from the virtual model.

45. The method according to any of the previous items, wherein said second gingival region is configured to be manufactured in a second material in a physical model manufactured from the virtual model.

46. The method according to any of the preceding items, wherein said second material is configured to be softer than said first material at ambient conditions.

47. The method according to any of the preceding items, wherein the virtual representation of the set of teeth is provided by scanning the set of teeth, such as by scanning the set of teeth by means of an intra-oral scanner or by scanning an impression of the set of teeth.

48. The method according to any of the preceding items, wherein the restoration comprises a full restoration or a part of a restoration, such as an abutment or a crown arranged on said abutment, an implant bar, or in principle any other indication used in relation to dental restorations.

49. The method according to any of the preceding items, wherein modifying the gingival part of the virtual model of the set of teeth comprises digitally cutting a portion of the gingiva away such that the volume of the restoration and the volume of the gingival part do not overlap.

50. The method according to any of the preceding items, wherein said second material is configured to be comprised in a removable unit in a physical model manufactured from the virtual model.

51. The method according to any of the preceding items, wherein the addition of material to the gingival part of the model comprises generating a gingiva mask.

52. The method according to any of the preceding items, wherein the gingival part after being configured to enable the correct positioning of a restoration is configured to follow the adjoining surface of the restoration.

53. The method according to any of the preceding items, wherein a void is provided between the adjoining surfaces of the restoration and the gingival part of the model.

54. The method according to any of items 51 to 53, wherein said gingiva mask comprises a first retention structure configured to mate with a second retention structure arranged on the gingival part of the model, such that the gingiva mask is arranged anatomically correct when said first and second retention structures mate.

55. The method according to any of the preceding items, wherein the gingival part of the model comprises an undercut region, in which said second gingival region is partly confined.

56. The method according to any of items 28 to 33, wherein the method comprises configuring the gingiva mask to comprise an opening, where the opening is configured to allow a restoration to access the gingival part arranged below the gingiva mask.

57. The method according to any of the preceding items, wherein a virtual hole is provided in said gingival part of the virtual model of the set of teeth, where said virtual hole is such that a corresponding hole in the physical model of the set of teeth is configured to mate with a part of said restoration configured to fit into the gingival part of the physical model of the set of teeth.

58: The method according to item 57, wherein said virtual hole is configured to allow an implant analog to be inserted manually in the corresponding hole of the physical model of the set of teeth.

59. The method according to item 57 or 58, wherein said virtual hole and/or said implant analog is configured such that said the implant analog can be inserted only in the correct anatomical position and orientation in the gingival part of the model.

60. The method according to any of items 57 to 59, wherein said implant analog is configured to have a shape with reduced cross sectional rotation symmetry, such as an N-fold symmetry, wherein N is an integer number below 25

61. The method according to any of the preceding items, wherein several steps in method are computer implemented.

62. The method according to any of the preceding items, wherein the gingival part of the virtual model of the set of teeth, is configured to provide that a corresponding ejection hole in the physical model of the set of teeth is in fluid connection with said hole such that a restoration or an implant analog can be accessed through said ejection hole to be ejected from the gingival part of the physical model of the set of teeth.

63. The method according to any of the preceding items, wherein the implant analog is configured to comprise a stop section with a smaller cross sectional area at its distal end, said stop section preferably being arranged centrally around the longitudinal axis of the implant analog.

64. The method according to any of the preceding items, wherein the virtual hole defined in the gingival part of the virtual model of the set of teeth is configured to provide that the corresponding hole in the physical model of the set of teeth has rounded edges at its distal end.

65. The method according to any of the preceding items, wherein the method comprises providing a cover which in cooperation with the first gingival region is configured to enclose the second gingival region.

66. The method according to item 65, wherein the cover comprises an opening configured to allow the injection of said second material into said second gingival region in a physical model manufactured from the virtual model of the teeth.

67. The method according to item 65 or 66, wherein a surface of the cover facing said second gingival region is shaped as said third surface.

68. The method according to any of the preceding items, wherein the method comprises designing and configuring the model to be manufactured by means of a specific manufacturing process.

69. A method of generating a virtual model of a set of teeth for manufacturing a physical model of the set of teeth, where the method comprises:
   obtaining a virtual model of the set of teeth, the model comprising a gingival part comprising a gingiva; and
   obtaining a virtual model of a restoration configured to be arranged in its anatomical correct position relative to said gingival part of the model;
where the surface of the gingiva defines a first surface at said restoration; and
   modifying the gingiva at said restoration such that the surface of the modifying gingiva defines a second surface at said restoration, wherein the second surface is configured to avoid an overlap between the volume of the restoration and the volume of the gingival part of the model.

70. A method of adjusting a virtual model of a set of teeth, where the virtual model of the set of teeth is for manufacturing a physical model of the set of teeth, where the method comprises:
   obtaining a pre-adjustment configuration of a virtual model of the set of teeth, the virtual model of the set of teeth comprising a gingival part; and
   obtaining a virtual model of a restoration configured to be arranged in its anatomical correct position relative to said gingival part of the model,
where the volume of the gingival part of the virtual model of the set of teeth and the volume of the virtual model of the restoration overlaps when the restoration is arranged in the anatomical correct position; and
   adjusting a portion of the gingival part of the virtual model of the set of teeth arranged at said restoration providing a post-adjustment configuration of the virtual model of the set of teeth, in which post-adjustment configuration the gingival part of the model is configured to avoid overlap between the volume of the virtual model of the restoration and the volume of the gingival part of the virtual model of the set of teeth.

71. The method according to item 70, wherein adjusting of the gingival part comprises configuring the shape of the gingival part such that the overlap between the volumes is avoided.

72. The method according to item 71 or 72, wherein the method comprises configuring the material of the gingiva at the restoration to be sufficiently soft such that a restoration may deform the gingival part.

73. A method of generating a physical model of a set of teeth, where the method comprises:
   obtaining at least one three dimensional representation of the set of teeth;
   generating and modifying a virtual model of the set of teeth from said at least one three dimensional representation, the virtual model of the set of teeth comprising a gingival part; and
   modifying the gingival part to enable insertion of a restoration in a region of the virtual model of the set of teeth configured for insertion of a restoration.
   manufacturing said physical model from said virtual model of the set of teeth.

74. The method according to any of the preceding items, wherein the method comprises manufacturing the physical model by means of three dimensional printing or milling.

75. The method according to item 73 or 74, wherein the physical model may be manufactured using a casting mold for casting an at least partly soft mould as part of the physical model of the set of teeth.

76. The method according to item 75, wherein a casting mold CAD model is generated as an impression of at least a part of the virtual model, said casting mold CAD model thereby comprising the negative geometry of the set of teeth.

77. The method according to any of items 73 to 76, wherein said second material is softer and more compressible than said first material at ambient conditions.

78. A physical model of a set of teeth, wherein the physical model is manufactured from a virtual model of the set of teeth generated and modified by the method according to any of items 1-77.

79. An ejection tool for ejecting a restoration according to any of the preceding items, when the restoration is arranged in a physical model of a set of teeth according to any of the preceding items.

80. The ejection tool according to item 79 comprising an elongated component which is adapted to fit into a through hole in the gingival part of the model.

81. The ejection tool according to item 79 or 80, comprising an elongated component which is adapted to fit into a blind hole and/or a through hole in the restoration.

The invention claimed is:

1. A method of generating and modifying a virtual model of a set of teeth, said set of teeth comprising a region configured for insertion of a restoration, the region being located in a gingival part of the set of teeth, the method comprises:
    obtaining at least one three dimensional representation of the set of teeth;
    generating a virtual model of the set of teeth from said three dimensional representation using a data processing system, where the virtual model of the set of teeth comprises a gingival part, said gingival part comprising a virtual region corresponding to said region configured for insertion of a restoration and at least part of the gingiva surrounding said region;
    obtaining a virtual model of said restoration;
    virtually inserting the virtual model of said restoration into said virtual region along an insertion path;
    identifying a circumference line for the dental restoration;
    defining an extrusion volume from the circumference line of the dental restoration and the insertion path; and
    using said data processing system to modify the gingival part of the virtual model of the set of teeth based on the virtual model of the restoration such that any overlap between a volume of the virtual model of said restoration and a volume of said gingival part of the virtual model of the set of teeth is removed, where the modifying comprises subtracting the extrusion volume from the virtual model of the set of teeth;
    wherein the virtual model can be used for manufacturing a physical model of the set of teeth.

2. The method according to claim 1, wherein an offset is provided between adjoining surfaces of the virtual model of the restoration and the gingival part of the virtual model of the set of teeth.

3. The method according to claim 1, wherein the gingival part of the generated virtual model of the set of teeth defines a first surface at the region configured for insertion of a restoration, and wherein the subtraction of the virtual model of the dental restoration from the virtual model of the set of teeth replaces the first surface with a second surface, where said second surface is shaped such that the virtual model of said restoration can be virtually arranged in said virtual implant region with no overlap with the modified virtual model of the set of teeth.

4. The method according to claim 3, wherein the method comprises defining a third surface forming an outer surface of the gingiva at the region configured for insertion of a restoration, such that the gingival part of the virtual model of the set of teeth is divided into a first and a second gingival region by the second surface with the second gingival region arranged between the second surface and the third surface, the second surface forming an interface between the first and the second gingival region.

5. The method according to claim 1, wherein the method comprises determining an insertion path for the restoration.

6. The method according to claim 1, wherein the method comprises digitally repositioning the gingival part of the model around the restoration.

7. The method according to claim 6, wherein digitally repositioning the gingival part of the virtual model of the set of teeth comprises digitally moving gingiva away from the virtual model of the restoration.

8. A method for manufacturing a physical model of a set of teeth comprising a region configured for insertion of a restoration, where the method comprises:
    obtaining at least one three dimensional representation of the set of teeth;
    generating a virtual model of the set of teeth from said three dimensional representation, where the virtual model of the set of teeth comprises a gingival part, said gingival part comprising a virtual region corresponding to said region configured for insertion of a restoration and at least part of the gingiva surrounding said region;
    obtaining a virtual model of said restoration;
    virtually inserting the virtual model of said restoration into said virtual region along an insertion path;
    identifying a circumference line for the dental restoration;
    defining an extrusion volume from the circumference line of the dental restoration and the insertion path; and
    modifying the gingival part of the virtual model of the set of teeth based on the virtual model of the restoration such that any overlap between a volume of the virtual model of said restoration and a volume of said gingival part of the virtual model of the set of teeth is removed, where the modifying comprises subtracting the extrusion volume from the virtual model of the set of teeth; and
    manufacturing said physical model from said virtual model of the set of teeth.

9. A method of generating and modifying a virtual model of a set of teeth, said set of teeth comprising a region configured for insertion of a restoration, the region being located in a gingival part of the set of teeth, the method comprises:
    obtaining at least one three dimensional representation of the set of teeth;
    generating a virtual model of the set of teeth from said three dimensional representation using a data processing system, where the virtual model of the set of teeth comprises a gingival part, said gingival part comprising a virtual region corresponding to said region configured for insertion of a restoration and at least part of the gingiva surrounding said region, and where the gingival part of the virtual model of the set of teeth defines a first surface at the region configured for insertion of a restoration;
    obtaining a virtual model of said restoration;
    virtually inserting the virtual model of said restoration into said virtual region along an insertion path;
    identifying a circumference line for the dental restoration;

defining an extrusion volume from the circumference line of the dental restoration and the insertion path; and modifying the gingival part of the virtual model of the set of teeth by using said data processing system to replace said first surface with a second surface which is shaped such that any overlap between a volume of the virtual model of said restoration and a volume of said gingival part of the virtual model of the set of teeth is removed, where the second surface at least partly is generated by subtracting the extrusion volume from the virtual model of the set of teeth;

where the virtual model can be used for manufacturing a physical model of the set of teeth.

10. A method of generating and modifying a virtual model of a set of teeth, said set of teeth comprising a region configured for insertion of a restoration, the region being located in a gingival part of the set of teeth, the method comprises:

obtaining at least one three dimensional representation of the set of teeth;

generating a virtual model of the set of teeth from said three dimensional representation using a data processing system, where the virtual model of the set of teeth comprises a gingival part, said gingival part comprising a virtual region corresponding to said region configured for insertion of a restoration and at least part of the gingiva surrounding said region;

obtaining a virtual model of said restoration;

virtually inserting the virtual model of said restoration into said virtual region along an insertion path;

identifying a circumference line for the dental restoration;

defining an extrusion volume from the circumference line of the dental restoration and the insertion path; and modifying the gingival part of the virtual model of the set of teeth based on the virtual model of the restoration and using said data processing system such that any overlap between a volume of the virtual model of said restoration and a volume of said gingival part of the virtual model of the set of teeth is removed, where modifying the gingival part of the virtual model comprises subtracting the extrusion volume from the virtual model of the set of teeth;

wherein the virtual model can be used for manufacturing a physical model of the set of teeth.

11. The method according to claim 10, wherein the gingival part of the generated virtual model of the set of teeth defines a first surface at the region configured for insertion of a restoration, and wherein the subtraction of the extrusion volume from the virtual model of the set of teeth replaces the first surface with a second surface, where said second surface is shaped such that the virtual model of said restoration can be virtually arranged in said virtual implant region with no overlap with the modified virtual model of the set of teeth.

12. The method according to claim 11, wherein the method comprises defining a third surface forming an outer surface of the gingiva at the region configured for insertion of a restoration, such that the gingival part of the virtual model of the set of teeth is divided into a first and a second gingival region by the second surface with the second gingival region arranged between the second surface and the third surface, the second surface forming an interface between the first and the second gingival region.

13. The method according to claim 11, wherein an offset is provided to the second surface such that a gap between the virtual model of the restoration and the offset second surface is formed.

14. The method according to claim 10, wherein the method comprises digitally repositioning the gingival part of the model around the restoration.

15. The method according to claim 14, wherein digitally repositioning the gingival part of the virtual model of the set of teeth comprises digitally moving gingiva away from the virtual model of the restoration.

16. The method according to claim 10, wherein an offset is provided to a surface of the virtual model of the set of teeth generated by the subtraction of the extrusion model such that a gap is formed between the virtual model of the restoration and the offset surface of the virtual model of the set of teeth.

* * * * *